United States Patent [19]
Curro et al.

[11] Patent Number: 5,658,639
[45] Date of Patent: Aug. 19, 1997

[54] METHOD FOR SELECTIVELY APERTURING A NONWOVEN WEB EXHIBITING SURFACE ENERGY GRADIENTS

[75] Inventors: John J. Curro, Cincinnati, Ohio; Douglas H. Benson, West Harrison, Ind.; James W. Cree, Cincinnati, Ohio; Luis E. Ravaglia, Caracas, Venezuela

[73] Assignee: The Proctor & Gamble Company, Cincinnati, Ohio

[21] Appl. No.: 536,227

[22] Filed: Sep. 29, 1995

[51] Int. Cl.$^6$ .............................. B05D 5/00; B32B 5/02; B32B 33/00
[52] U.S. Cl. .................... 428/131; 427/243; 427/275; 427/278; 427/288; 428/195; 604/381; 604/382
[58] Field of Search .................... 427/243, 275, 427/278, 288; 428/131, 195, 290; 604/381, 382

[56] References Cited

U.S. PATENT DOCUMENTS 3,949,127  4/1976  Ostermeier et al. ............ 428/137

FOREIGN PATENT DOCUMENTS

WO95/32327  11/1995  WIPO .............. D04H 1/70

Primary Examiner—James C. Cannon
Attorney, Agent, or Firm—Kevin C. Johnson; Steven W. Miller; Jacobus C. Rasser

[57] ABSTRACT

The present invention pertains, in a preferred embodiment, to a method for selectively aperturing a nonwoven web exhibiting a plurality of surface energy gradients. The method includes the steps of: providing a nonwoven web of fibers exhibiting a surface energy, the nonwoven web having a first surface, a second surface and a plurality of fluid passageways placing the first and second surfaces in fluid communication with one another; applying a surface treatment to the first surface of the nonwoven web, the surface treatment having a surface energy less than the surface energy of the fibers of the nonwoven web creating a plurality of surface energy gradients defined by discontinuous, spaced regions which are adapted to exert a force on a fluid contacting the first surface, such that the fluid will be directed toward the fluid passageways for transportation away from the first surface and in the direction of the second surface; weakening the nonwoven web at a plurality of locations creating a plurality of weakened, melt-stabilized locations; and applying a tensioning force to the nonwoven web to cause the nonwoven web to rupture at the plurality of weakened, melt-stabilized locations creating a plurality of apertures in the nonwoven web coincident with the plurality of weakened, melt-stabilized locations. The web is particularly well suited for use as a topsheet on a disposable absorbent article.

29 Claims, 12 Drawing Sheets

METHOD FOR SELECTIVELY APERTURING A NONWOVEN WEB EXHIBITING SURFACE ENERGY GRADIENTS

FIELD OF THE INVENTION

The present invention relates to an apertured nonwoven web which is suitable for use as a fluid transport mechanism and a method for making the same. In particular, the apertured nonwoven web is designed to facilitate fluid transport in a preferential direction from one surface toward another surface and resist fluid transport in the opposite direction.

BACKGROUND OF THE INVENTION

Nonwoven webs formed by nonwoven extrusion processes such as, for example, meltblowing processes and spunbonding processes may be manufactured into products and components of products so inexpensively that the products could be viewed as disposable after only one or a few uses. Representatives of such products include disposable absorbent articles, such as diapers, incontinence briefs, training pants, feminine hygiene garments, and the like.

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many basic designs are known to the art.

A typical absorbent article includes a liquid pervious topsheet, a liquid impervious backsheet joined to the topsheet, and an absorbent core positioned between the topsheet and the backsheet. Nonwoven webs are often used as topsheets on disposable absorbent articles as they are liquid pervious and provide a skin friendly surface. However, in certain uses nonwoven webs do not function all that well as a topsheet as body exudates sometimes hang-up or get caught in the nonwoven web and thus, become trapped against the wearer's skin. One solution to the aforementioned problem is to provide apertures in the nonwoven web so that body exudates may readily penetrate through the nonwoven web and into the underlying absorbent core. Unfortunately, certain techniques used to form apertured nonwoven webs are either costly, create an undesirable harsh feeling against the wearer's skin, or are subject to tearing, particularly when the apertured nonwoven web is to be used as a topsheet on a disposable absorbent article.

As used herein, the term "nonwoven web", refers to a web that has a structure of individual fibers or threads which are interlaid, but not in any regular, repeating manner. Nonwoven web have been, in the past, formed by a variety of processes, such as, for example, meltblowing processes, spunbonding processes and bonded carded web processes.

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fiber", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

As used herein, the term "elastic", refers to any material which, upon application of a biasing force, is stretchable, that is, elongatable, at least about 60 percent (i.e., to a stretched, biased length, which is at least about 160 percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretching force.

As used herein, the term "nonelastic" refers to any material which does not fall within the definition of "elastic" above.

As used herein, the term "extensible" refers to any material which, upon application of a biasing force, is elongatable, at least about 50 percent without experiencing catastrophe failure.

As used herein, the term "melt-stabilized" refers to portions of a nonwoven web which have been subjected to localized heating and/or localized pressure to substantially consolidate the fibers of the nonwoven web into a stabilized film-like form.

As used herein, the term "passageway" is intended to encompass enclosed or at least partially enclosed structures or channels which may communicate fluids. The term fluid passageway is thus intended to encompass the terms "aperture", "channel", "capillary", as well as other similar terms.

SUMMARY OF THE INVENTION

The present invention pertains, in a preferred embodiment, to a method for selectively aperturing a fluid pervious nonwoven web which exhibits a plurality of surface energy gradients. The method comprises the steps of:

providing a fluid-pervious nonwoven web of fibers exhibiting a surface energy, the nonwoven web has a first or wearer-contacting surface, a second or garment-facing surface, and a plurality of fluid passageways placing the first and second surfaces in fluid communication with one another;

applying a surface treatment to the first surface of the nonwoven web, the surface treatment having a surface energy less than the surface energy of the fibers of the nonwoven web, thereby creating a plurality of surface energy gradients defined by discontinuous, spaced regions which are adapted to exert a force on a fluid contacting the first surface, such that fluid will be directed toward the fluid passageways for transportation away from the first surface and in the direction of the second surface;

weakening the nonwoven web at a plurality of locations to create a plurality of weakened, melt-stabilized locations; and applying a tensioning force to the nonwoven web to cause the nonwoven web to rupture at the plurality of weakened, melt-stabilized locations creating a plurality of apertures in the nonwoven web coincident with the plurality of weakened, melt-stabilized locations. The tensioning force is preferably applied by subjecting the nonwoven web to incremental stretching.

The nonwoven web is particularly well suited for use as a topsheet on a disposable absorbent article. The first and second surfaces are separated from one another by an intermediate portion. The first surface of the nonwoven web provides a structure which exhibits a surface energy less than the surface energy of the intermediate portion. In a preferred embodiment, the nonwoven web exhibits a plurality of regions of comparatively low surface energy which define surface energy gradients where they interface with higher surface energy web surfaces.

More particularly, the present invention pertains to a fluid-pervious nonwoven web having a plurality of small-scale surface energy gradients which are oriented and located so as to effectively transport fluid away from the first or wearer-contacting surface. The web essentially retains its visual, tactile, and physical properties of the substrate material while achieving the desired surface energy properties.

Nonwoven webs according to the present invention preferably include discontinuous, spaced regions defining small scale surface energy gradients on the first surface to aid in small scale fluid movement toward capillary entrances for transport away from the first surface. Such webs also preferably include small scale surface energy gradients normal to the first surface within a capillary structure to aid in moving fluid away from the first surface and into the capillaries for capillary fluid transport.

The present invention also pertains to absorbent articles which preferably include a topsheet, a backsheet secured to the topsheet, and an absorbent core positioned between the topsheet and the backsheet, wherein the topsheet exhibits surface energy gradients according to the present invention.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE PRESENT INVENTION

Figure 1:
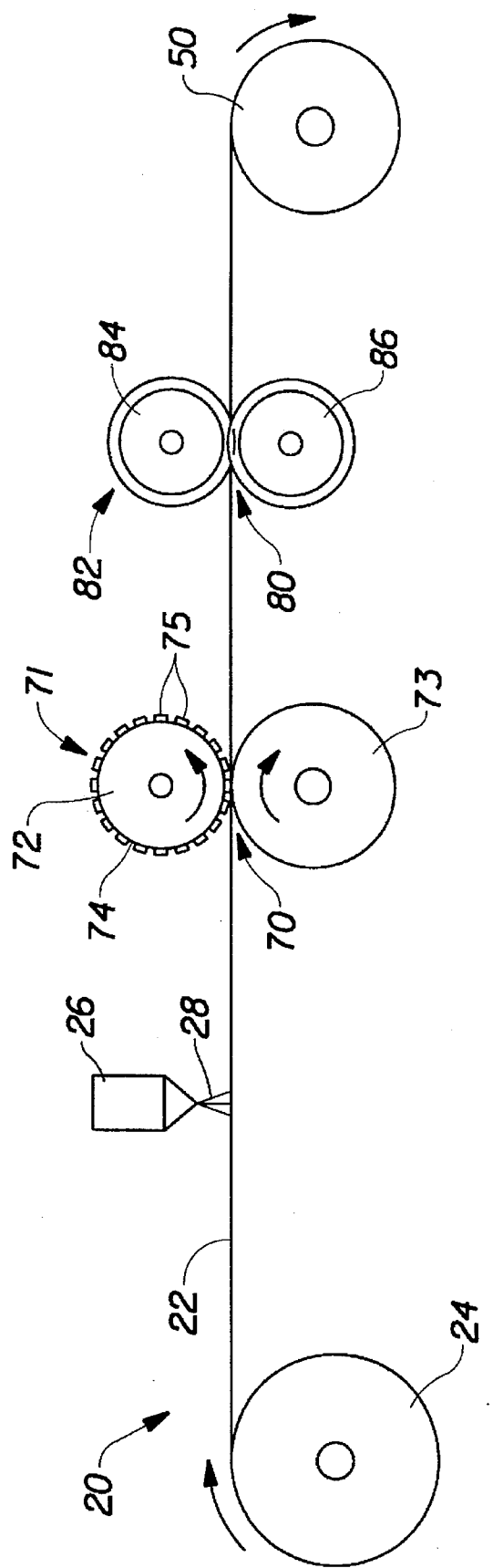
FIG. 1 is a schematic representation of an exemplary process for forming a nonwoven web exhibiting surface energy gradients of the present invention.

Referring to FIG. 1, there is schematically illustrated at 20 a process for selectively aperturing a nonwoven web exhibiting surface energy gradients of the present invention which is suitable for use as a topsheet on a disposable absorbent article.

According to the present invention, a nonwoven web 22 is unwound from a supply roll 24 and travels in a direction indicated by the arrows associated therewith as the supply roll 24 rotates in the direction indicated by the arrows associated therewith. The nonwoven web 22 passes beneath sprayer 26 which directs a surface treatment 28 onto a surface of the nonwoven web 22.

The nonwoven web 22 may be formed by known nonwoven extrusion processes, such as, for example, known meltblowing processes or known spunbonding processes, and passed directly beneath sprayer 26 without first being stored on a supply roll.

The nonwoven web 22 may be extensible, elastic, or nonelastic. The nonwoven web 22 may be a spunbonded web, a meltblown web, or a bonded carded web. If the nonwoven web is a web of meltblown fibers, it may include meltblown microfibers. The nonwoven web 22 may be made of natural fibers such as wood, cotton, or rayon, or synthetic fibers such as polypropylene, polyethylene, polyester, ethylene copolymers, propylene copolymers, and butene copolymers, bicomponent fibers, or combinations of natural and synthetic fibers.

The nonwoven web 22 may be a multilayer material having, for example, at least one layer of a spunbonded web joined to at least one layer or a meltblown web, a bonded carded web, or other suitable material. Alternatively, the nonwoven web may be a single layer or material, such as, for example a spunbonded web, a bonded carded web, or a meltblown web.

The nonwoven web 22 may also be a composite made up of a mixture of two or more different fibers or a mixture of fibers and particles. Such mixtures may be formed by adding fibers and/or particulates to the gas stream in which the meltblown fibers are carried so that an intimate entangled co-mingling of meltblown fibers and other materials, e.g., wood pulp, staple fibers and particles occurs prior to collection of the meltblown fibers upon a collecting device to form a coherent web of randomly dispersed meltblown fibers and other materials.

The nonwoven web of fibers should be joined by bonding to form a coherent web structure. Suitable bonding techniques include, but are not limited to, chemical bonding, thermobonding, such as point calendering, hydroentangling, and needling.

The surface treatment 28 is applied to one surface of the nonwoven web 22 in FIG. 1 utilizing sprayer 26. Surface treatments may also be applied to one surface of the nonwoven web by other techniques known in the art such as screen printing, gravure printing, dip coating, etc.

Figure 2:
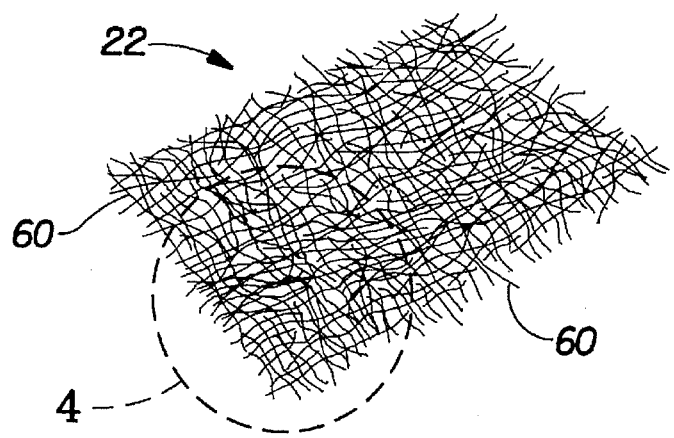
FIG. 2 is an enlarged, partially segmented, perspective illustration of a nonwoven web of the present invention.
Figure 3:
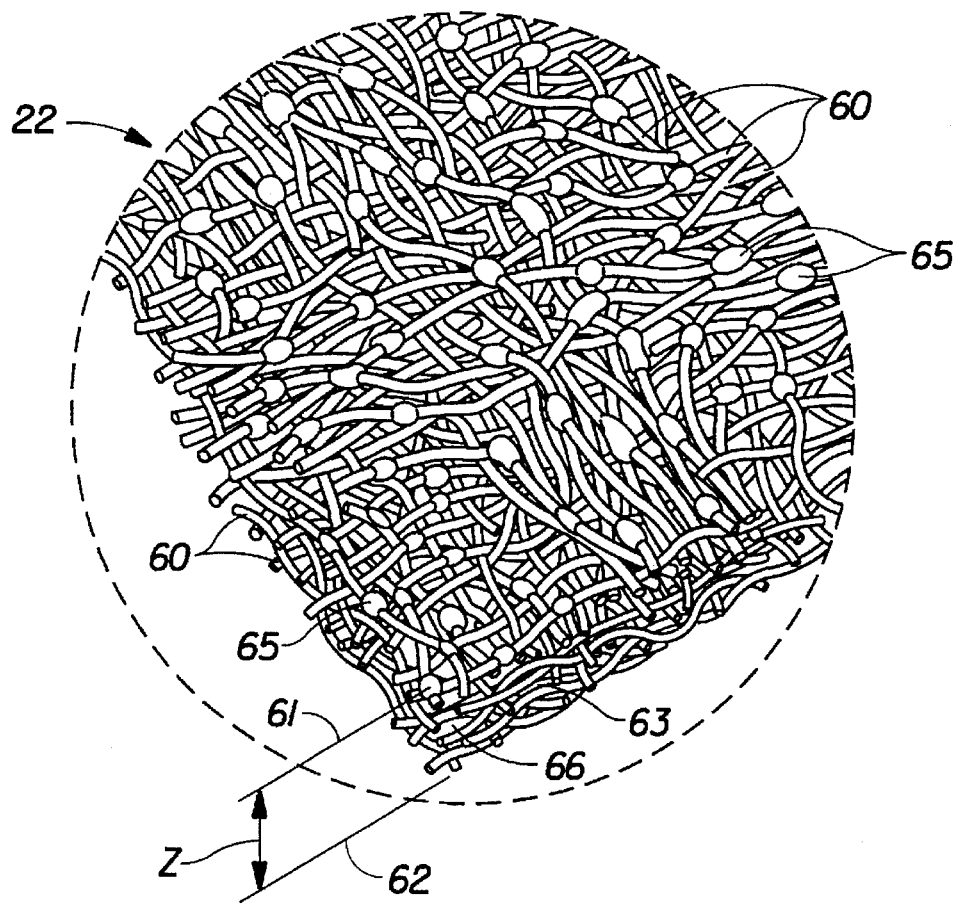
FIG. 3 is a further enlarged, partial view of the nonwoven web of FIG. 2.

Referring now to FIGS. 2 and 3, there is shown a perspective view of a nonwoven web 22 in accordance with the present invention having the surface treatment applied to one surface thereof. Nonwoven web 22 is a fluid pervious nonwoven web comprised of individual fibers 60.

The nonwoven web 22 preferably has a first or upper surface 61 and a second surface or lower 62. The first surface 61 is spaced from the second surface 62 by an intermediate portion 63. The nonwoven web 22 preferably includes a plurality of passageways 66 placing the first and second surfaces in fluid communication with one another.

The first surface 61 preferably has a plurality of regions 65 which exhibit a comparatively low surface energy and preferably comprise a low surface energy surface treatment. Preferably, the regions 65 have a relatively low surface energy and a relatively low work of adhesion as compared to the fibers 60 of the nonwoven web which have a relatively high surface energy and a relatively high work of adhesion. Accordingly, the treated nonwoven web 22 exhibits a plurality of surface energy gradients defined by the boundaries of regions 65, i.e., the interfaces between regions 65 and the surrounding fiber surfaces.

As depicted in FIG. 3, the relationship of the regions 65 to the surface topography (including individual fibers protruding upward from the upper surface of the web) is believed to be an important aspect of the present invention. Note the intermittent or discontinuous, spaced nature of the regions with regard to the surface direction of the web and the thickness direction of the web, particularly since the surface treatment as depicted in FIG. 3 is actually a plurality of discrete particles, droplets, or globules which coat portions of individual fibers rather than a bridging or masking of the fibers which would occlude the interfiber pores. As discussed above, this discontinuity results in the generation of a plurality of small-scale surface energy gradients which are believed to be beneficial from a fluid-movement perspective.

Also clearly depicted in FIG. 3 is the penetration of the surface treatment into and below the first surface 61 of the nonwoven web 22. While the majority of the regions 65 are concentrated near the first surface 61 itself, the treated regions extend downward through the web on a fiber-by-fiber basis to achieve a penetration into the intermediate portion 63. Preferably, regions 65 are concentrated near the first surface 61 and decrease in frequency (increase in spacing) with increasing distance from the first surface, such that more low surface energy regions, and hence more surface energy gradients, are generated at or near the first surface 61 for greater effect on fluids on or near the first surface. On average, therefore, the upper regions of the web near the first surface would exhibit a lower average surface energy than that exhibited by lower regions of the web nearer to the second surface.

The non-occlusion of the interfiber capillaries is believed to be important such that sufficient fluid passageways remain open for fluid transmission to the underlying structure. If the surface treatment is applied to heavily it may tend to occlude the interfiber capillaries thereby blocking fluid transmission to the underlying structure.

Although the foregoing discussion has focused on a true nonwoven substrate, it should be understood that the concepts of the present invention could be readily applied to woven or hybrid woven/nonwoven substrates in similar fashion. In doing so, recognition of the degree of porosity present in the interwoven structure is necessary to extrapolate the foregoing discussion regarding the porosity and interfiber capillary spacing of the nonwoven webs to interwoven structures.

In addition, the definition of "fiber" as utilized herein is intended to also encompass a type of fiber structure commonly referred to as a "capillary channel fiber", that is, a fiber having a capillary channel formed therein. Suitable fibers of this variety are described in greater detail in U.S. Pat. Nos. 5,200,248, 5,242,644, and 5,356,405, all of which issued to Thompson et al. on Apr. 6, 1993, Sep. 7, 1993, and Oct. 18, 1994, respectively, the disclosures of which are hereby incorporated herein by reference. Fibrous structures formed of such fibers may exhibit not only inter-fiber capillaries and spaces, but also intra-fiber capillary structures.

Figure 4:
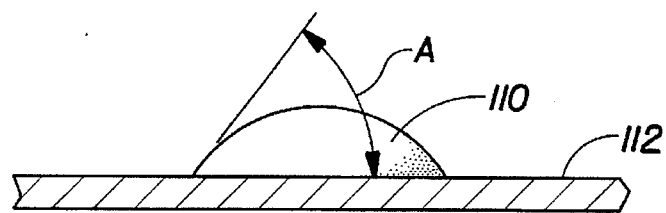
FIG. 4 is an enlarged cross-sectional view of a droplet of liquid on a solid surface, where angle A illustrates the contact angle of the liquid with the solid surface.

In accordance with the present invention, the first or wearer-contacting surface 61 of nonwoven web 22 is relatively non-wettable compared to the relatively wettable intermediate portion 63. A useful parameter of wettability is the contact angle that a drop of liquid (gas-liquid interface) makes with the solid surface (gas-solid interface). Typically, a drop of liquid 110 placed on a solid surface 112 makes a contact angle, A, with the solid surface, as seen in FIG. 4. As the wettability of the solid surface by the liquid increases, the contact angle, A, decreases. As the wettability of the solid surface by the liquid decreases, the contact angle, A, increases. The liquid-solid contact angle may be determined from techniques known in the art, such as those described in greater detail in *Physical Chemistry of Surfaces*, Second Edition, by Arthur W. Adamson (1967), F. E. Bartell and H. H. Zuidema, *J. Am. Chem. Soc.*, 58, 1449 (1936), and J. J. Bikerman, *Ind. Eng. Chem., Anal. Ed.*, 13, 443 (1941), each of which are hereby incorporated herein by reference. More recent publications in this area include Cheng, et at., *Colloids and Surfaces* 43:151–167 (1990), and Rotenberg, et at., *Journal of Colloid and Interface Science* 93(1):169–183 (1983), which are also hereby incorporated herein by reference.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a fluid (hydrophilic) when the fluid tends to spread spontaneously across the surface. Conversely, a surface is considered to be "hydrophobic" if the fluid does not tend to spread spontaneously across the surface.

The contact angle depends on surface inhomogeneities (e.g., chemical and physical properties, such as roughness), contamination, chemical/physical treatment of or composition of the solid surface, as well as the nature of the liquid and its contamination. The surface energy of the solid also influences the contact angle. As the surface energy of the solid decreases, the contact angle increases. As the surface energy of the solid increases, the contact angle decreases.

The energy required to separate a liquid from a solid surface (e.g., a film or fiber) is expressed by equation (1):

$$W=G(1+\cos A) \quad (1)$$

where:

W is the work of adhesion measured in $erg/_{cm}2$,

G is the surface tension of the liquid measured in dyne/cm, and

A is the liquid-solid contact angle measured in degrees. With a given liquid, the work of adhesion increases with the cosine of the liquid-solid contact angle (reaching a maximum where the contact angle A is zero).

Work of adhesion is one useful tool in understanding and quantifying the surface energy characteristics of a given surface. Another useful method which could be utilized to characterize the surface energy characteristics of a given surface is the parameter labeled "critical surface tension", as discussed in H. W. Fox, E. F. Hare, and W. A. Zisman, *J. Colloid Sci.* 8, 194 (1953), and in Zisman, W. A., *Advan. Chem. Series No.* 43, Chapter 1, American Chemical Society (1964), both of which are hereby incorporated herein by reference.

Illustrated below in Table 1 is the inverse relationship between contact angle and work of adhesion for a particular fluid (e.g., water), whose surface tension is 75 dynes/cm.

TABLE 1

| A (degrees) | cos A | 1+ cos A | W (erg/cm²) |
|---|---|---|---|
| 0 | 1 | 2 | 150 |
| 30 | 0.87 | 1.87 | 140 |
| 60 | 0.5 | 1.50 | 113 |
| 90 | 0 | 1.00 | 75 |
| 120 | −0.5 | 0.5 | 38 |
| 150 | −0.87 | 0.13 | 10 |
| 180 | −1 | 0 | 0 |

As depicted in Table 1, as the work of adhesion of a particular surface decreases (exhibiting a lower surface energy of the particular surface), the contact angle of the fluid on the surface increases, and hence the fluid tends to "bead up" and occupy a smaller surface area of contact. The reverse is likewise true as the surface energy of a given surface decreases with a given fluid. The work of adhesion, therefore, influences interfacial fluid phenomena on the solid surface.

Figure 5:
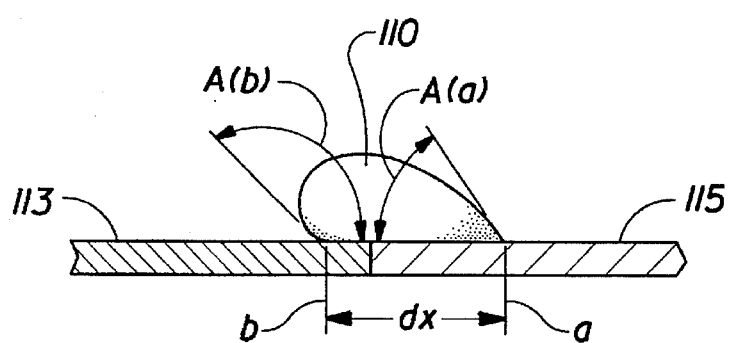
FIG. 5 is an enlarged cross-sectional view of a droplet of liquid on a solid surface having two different surface energies, thus exhibiting two different contact angles A(a) and A(b)

More importantly, in the context of the present invention, surface energy gradients or discontinuities have been found to be useful in promoting fluid transport. FIG. 5 illustrates a droplet of fluid 110 which is located on a solid surface having two regions 113 and 115 having differing surface energies (indicated by the different cross-hatching for illustrative purposes). In the situation illustrated in FIG. 5, region 113 exhibits a comparatively lower surface energy than region 115, and hence a reduced wettability for the fluid of the droplet than region 115. Accordingly, the droplet 110 produces a contact angle A(b) at the edge of the droplet contacting region 113 which is greater than the contact angle A(a) produced at the edge of the droplet contacting region 115. It should be noted that although for graphic rarity the points "a" and "b" lie in a plane, the distance "dx" between points "a" and "b" need not be linear, instead representing the extent of droplet/surface contact regardless of the shape of the surface. Droplet 110 thus experiences a surface energy imbalance and hence an external force due to the differences in the relative surface energies (i.e., the surface energy gradient or discontinuity) between regions 113 and 115, which can be represented by the equation (2):

$$dF=G[\cos A(a) - \cos A(b)]dx$$

where:

dF is the net force on the fluid droplet, dx is the distance between the reference locations "a" and "b", G is as defined previously, and A(a), and A(b) are the contact angles A at locations "a" and "b", respectively.

Solving equation (1) for cos A(a) and cos A(b) and substituting into equation (2) yields equation (3):

$$dF=G[(W(a)/G-1)-(W(b)/G-1)]dx \quad (3)$$

Equation (3) can be simplified to equation (4):

$$dF=(W(a)-W(b))dx \quad (4)$$

The importance of the differential in surface energy between the two surfaces is clearly depicted in equation (4), as is the directly proportional effect that changes in the magnitude of the differential in work of adhesion would have on the magnitude of the force.

More detailed discussions of the physical nature of surface energy effects and capillarity may be found in *Textile Science and Technology*, Volume 7, *Absorbency*, edited by Portnoy K. Chatterjee (1985), and *Capillarity, Theory and Practice*, Ind. Eng. Chem. 61,10 (1969) by A. M. Schwartz, which are hereby incorporated herein by reference.

Accordingly, the force experienced by a droplet will cause movement in the direction of the higher surface energy. For simplicity and graphic clarity, the surface energy gradient or discontinuity has been depicted in FIG. 5 as a single, sharp discontinuity or boundary between well-defined regions of constant but differing surface energy. Surface energy gradients may also exist as a continuous gradient or a step-wise gradient, with the force exerted on any particular droplet (or portions of such droplet) being determined by the surface energy at each particular area of droplet contact.

As used herein, the term "gradient" when applied to differences in surface energy or work of adhesion is intended to describe a change in surface energy or work of adhesion occurring over a measurable distance. The term "discontinuity" is intended to refer to a type of "gradient" or transition, wherein the change in surface energy occurs over an essentially zero distance. Accordingly, as used herein all "discontinuities" fall within the definition of "gradient".

Also, as used herein the terms "capillary" and "capillarity" are used to refer to passageways, apertures, pores, or spaces within a structure which are capable of fluid transport in accordance with the principles of capillarity generally represented by the Laplace equation (5):

$$p=2G(\cos A)/R$$

where:

p is the capillary pressure;

R is the internal radius of the capillary (capillary radius); and

G and A are as defined above.

As noted in *Penetration of Fabrics* by Emery I. Valko, found in Chapter III of *Chem. Aftertreat. Text.* (1971), pp. 83–113, which is hereby incorporated herein by reference, for A=90°, the cosine of A is zero and there is no capillary pressure. For A>90°, the cosine of A is negative and the capillary pressure opposes the entry of fluid into the capillary. Hence, the capillary walls must be of a hydrophilic nature (A<90°) for capillary phenomena to occur. Also, R must be sufficiently small for p to have a meaningful value, since as R increases (larger aperture/capillary structure) the capillary pressure decreases.

Perhaps at least as important as the presence of surface energy gradients is the particular orientation or location of the gradients themselves with respect to the orientation and location of the capillaries or fluid passageways themselves. More particularly, the surface energy gradients or discontinuities are located in relation to the capillaries such that fluid cannot reside on the first or upper surface without contacting at least one surface energy gradient or discontinuity and thus experience the driving force accompanying the gradient. Fluid moved to or otherwise present at a capillary entrance will preferably contact at least one Z-direction gradient or discontinuity present in the capillary itself near the capillary entrance, and thus experience the Z-direction driving force to drive the fluid into the capillary where capillary forces take over to move the fluid away from the first surface. In a preferred configuration, the capillaries preferably exhibit a low surface energy entrance length and an otherwise higher surface energy capillary wall or surface such that the surface energy gradient or discontinuity is a comparatively small but finite distance below the first surface. In such a location the discontinuity or gradient is positioned such that fluid in contact with the first surface at the edge of the capillary or over the open end of the capillary will have a lower surface or meniscus which will extend downwardly into the open end of the capillary where it will contact the discontinuity.

Figure 6:
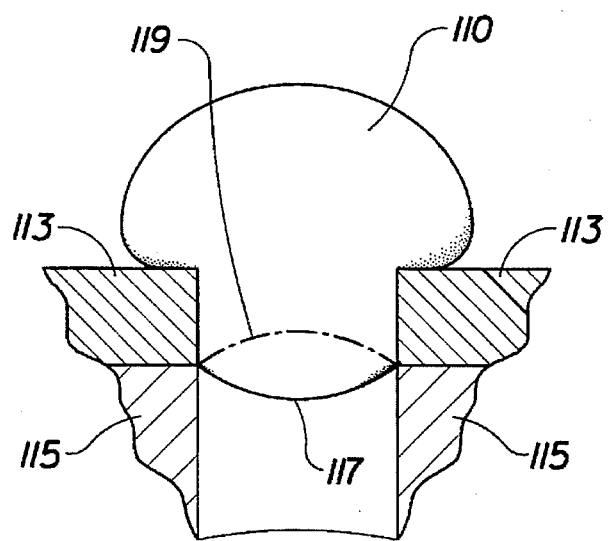
FIG. 6 is an enlarged cross-sectional view of a droplet of liquid located adjacent a generic capillary exhibiting a surface energy gradient.

By way of further explanation of this principle, FIG. 6 depicts a droplet 110 of a fluid which is located over a generic capillary or fluid passageway. This representation is intended to be sufficiently generic as to represent the concept expressed herein without being limited to a particular web material, design, or construction. Analogously to FIG. 5, the capillary is formed so as to present surfaces as 113 and 115 having different surface energies (indicated by the different cross-hatching for illustrative purposes). As in FIG. 5, the surface energy of surface 113 is at a predetermined level which is comparatively low in comparison with that of surface 115, such that surface 113 is regarded as hydrophobic. Accordingly, the droplet edges in contact with surface 113 will exhibit a relatively larger contact angle A such that the droplet edges make a sharp departure from the interface with surface 113. Surface 115, on the other hand, has a comparatively higher surface energy in comparison with surface 113.

In the situation depicted in FIG. 6, the droplet 110 is located over and extends partially into the entrance of the capillary in a condition where the surface tension forces and gravitational forces are roughly in equilibrium. The lower portion of the droplet which is within the capillary forms a meniscus 117, with its edges in contact with the capillary wall in the region 113 having hydrophobic surface energy characteristics. The surface energy gradient, discontinuity, or transition between surfaces 113 and 115 is particularly determined so as to contact the lower portion of the droplet in the vicinity of the edge of the meniscus 117. The orientation of the droplet and depth of the meniscus of the droplet are determined by such factors as fluid viscosity, fluid surface tension, capillary size and shape, and the surface energy of the upper surface and capillary entrance.

At the instant when the droplet positions itself over the capillary entrance and the lower edge of the droplet contacts the Z-direction surface energy gradient, discontinuity, or transition between surfaces 113 and 115, the meniscus 117 which is of a convex shape reverts to a concave-shaped meniscus such as meniscus 119 depicted in dot-dash line form. When the meniscus changes to a concave form such as meniscus 119, the fluid wets the capillary wall in the vicinity of the upper region of the hydrophilic surface 115 and the fluid experiences an external force due to the surface energy differential described above in equation (3). The combined surface energy and capillary pressure forces thus act in concert to draw the fluid into the capillary for capillary fluid transport away from the first surface. As the fluid droplet moves downward into the capillary, the comparatively low surface energy nature of the surface 113 at the upper region of the capillary minimizes the attraction of the fluid to the upper surface and minimizes drag forces on the droplet, reducing the incidence of fluid hang-up or residue on or near the upper surface.

Water is used as a reference liquid throughout only as an example for discussion purposes, and is not meant to be limiting. The physical properties of water are well-established, and water is readily available and has generally uniform properties wherever obtained. The concepts regarding work of adhesion with respect to water can easily be applied to other fluids such as blood, menses and urine, by taking into account the particular surface tension characteristics of the desired fluid.

Referring again to FIG. 3, while the first or wearer-contacting surface 61 of nonwoven web 22 has a relatively low surface energy and a relatively low work of adhesion for a given fluid (e.g., water, or bodily fluids such as menses), the intermediate portions 63 of the nonwoven web 22 preferably have a relatively high surface energy and a relatively high work of adhesion for a given fluid. Since the intermediate portions 63 of the nonwoven web 22 have a relatively higher surface energy as compared to the first surface 61, the intermediate portions 63 are more wettable than the first surface 61.

The second surface 62 of the nonwoven web 22 preferably has a higher surface energy and a higher work of adhesion for fluid than that of the first surface 61. The surface energy and work of adhesion for fluid of second surface 62 may be the same as that of the intermediate portion 63. In a preferred embodiment, the surface energy and work of adhesion for fluid of the second surface 62 are relatively higher than that of the intermediate portion 63.

By having a web with a surface energy gradient formed by structures creating a relatively low surface energy adjacent the portion of the web which will be placed adjacent to and in contact with the wearer's skin (i.e., the first surface 61), and a relatively higher surface energy portion located away from contact with the wearer's skin (i.e., the intermediate portion 63), the nonwoven web 22 will be capable of moving a drop of liquid from the portion of the web exhibiting the relatively lower surface energy to the portion of the web exhibiting the relatively higher surface energy. The motion of the drop of liquid is induced by the contact angle differential between the lower surface energy portion and the higher surface energy portion which results in an imbalance in surface tension force acting on the solid-liquid contact plane. It is believed that this resulting surface energy gradient, which enhances the fluid handling properties of the web 22 of the present invention and which makes the web well suited for use as a topsheet on an absorbent article.

In addition to the enhanced fluid handling properties, by designing the web so that its relatively lower surface energy portion can be placed in contact with the wearer's skin, the adhesion between the skin and the web is reduced by decreasing the capillary force generated by occlusive body fluids located between the first surface of the web and the wearer's skin. By providing a structure with reduced adhesion between the wearer's skin and the web, the sensation or impression of stickiness is also reduced.

The potential for rewet is also reduced by having a topsheet with a surface energy gradient according to the aforementioned description. As use forces tend to force the collected fluid to rewet or be squeezed out of the pad (e.g., squeezed by compression from the absorbent core towards the first surface of the topsheet), such undesirable movement will be resisted by the first surface of the topsheet which has a relatively low surface energy to repel the fluid as it attempts to make its way out of the pad through the openings in the topsheet.

Furthermore, fluid is able to enter the topsheet more quickly due to the driving forces of the surface energy gradients of the topsheet. Fluid is moved in the "Z" direction toward the second surface of the topsheet via the surface energy gradients from the first surface energy to the relatively higher surface energy of the intermediate portions of the topsheet toward the absorbent core.

With regard to the surface energy gradients of the present invention, it is important to remember that the upper and lower bounds of any such gradient are relative with respect to one another, i.e., the regions of the web whose interface defines a surface energy gradient need not be on different sides of the hydrophobic/hydrophilic spectrum. That is to say, a gradient may be established by two surfaces of diverse degrees of hydrophobicity or diverse degrees of hydrophilicity, and need not necessarily be established with regard to a hydrophobic surface and a hydrophilic surface. Notwithstanding the foregoing, it is preferred that the upper surface of the web have a comparatively low surface energy, i.e., that it be generally hydrophobic, in order to maximize the driving force imparted to the incoming fluid and minimize the overall wettability of the wearer-contacting surface.

It should be noted that with regard to FIG. 3, the size and shape of regions 65 have been exaggerated in resolution and thickness for graphic clarity. The randomness and irregularity of such depositions or treatments exceed the limitations of graphic depiction, and hence the illustrations herein are intended to be illustrative and not limiting. Accordingly, the regions 65 depicted in FIG. 3 are preferably also interspersed by even smaller regions which are too small and random to be depicted adequately in such an illustration.

The surface energy gradients of the present invention therefore exist in a unique relationship to the surface features and/or textures of a fluid pervious web made in accordance herewith. As depicted in FIG. 3, the surface energy gradients are preferably constructed by forming regions 65 of low surface energy which interface with surrounding regions of the web which are of a comparatively higher surface energy. Therefore, each region 65 generates a surface energy gradient at its boundary. Accordingly, the greater the number of regions 65, the greater the number of individual surface energy gradients. Regions 65 are preferably discontinuous (i.e., not entirely encapsulating the web) and spaced, leaving intervening regions of higher surface energy.

At each gradient, a droplet contacting both surfaces experiences a driving force which imparts some degree of motion to the fluid and reduces the likelihood of fluid stagnation or hangup, particularly on surface topography. Although the regions 65 could be applied in a predetermined pattern, the regions 65 are preferably randomly oriented on the web surfaces, with the randomness increasing the likelihood that the surface energy gradients will be properly positioned so as to affect any particular droplet or quantity of fluid. Randomness is desirable not only across the first surface of the web, but also within the fluid passageways themselves. Accordingly, any particular passageway may exhibit multiple surface energy gradients defined by regions 65 which may also be located at differing locations in the Z-direction from the first surface. Also, particular fluid passageways may exhibit more or less regions 65 than other fluid passageways, and regions 65 may also be located so as to entirely reside within fluid passageways (i.e., be entirely located between the first and second surfaces).

The regions 65 are also preferably discontinuous in nature with respect to the surface directionality of the web. The discontinuity of a hydrophobic surface treatment applied to a less hydrophobic (or more hydrophilic) substrate such as the web surface results in a pattern of small-scale surface energy gradients in the plane of the surface. Such gradients are to be distinguished from large-scale X-Y gradients of a zonal nature by their smaller relative size vis-a-vis average droplet size and size of web surface details. Accordingly, as used herein the term "small-scale" is intended to refer to surface features, topography, or surface energy gradients which are smaller in magnitude than the average size of a droplet of fluid on the surface in question. Average droplet size is a readily determinable characteristic which may be obtained from empirical observations for given fluids and surfaces.

Without wishing to be bound by theory, improvements in fluid pass-through characteristics are believed to be realized by a reduction in residence time of fluid on the upper surfaces of the web, as well as the movement of fluid from the upper surface into the capillaries for capillary fluid transport. Therefore, it is believed to be desirable for the initial fluid contacting surface of the web to facilitate small-scale movement of fluid (as opposed to larger lateral movement across the web surface) toward the nearest available capillary and then rapidly downward into the underlying structure. The surface energy gradients of the present invention provide the desired Z-direction driving force, as well as the X-Y driving force to impart the desired small-scale fluid movement.

The plurality of small-scale surface energy gradients exhibited by such webs are believed to be beneficial from a fluid-movement perspective. The small-scale gradients aid in the lateral or X-Y movement of fluid droplets formed on the web surface.

In addition, the regions 65, which are smaller in their surface-wise extent than the typical size of the droplet, stream, or rivulet of bodily fluid incident thereon, subject the droplet, stream, or rivulet of bodily fluid to destabilizing forces due to the inevitability of the fluid bridging a surface energy gradient or discontinuity.

While the surface energy gradients of the type herein described could advantageously be employed on non-capillary structures, including the surfaces of such structures as two-dimensional ("planar") films, in accordance with the present invention, it is preferable to employ both small scale X-Y surface energy gradients and small scale Z-direction surface energy gradients of the type herein described to achieve maximum disturbance of fluid and droplet equilibrium and thus minimize fluid residence time and hang-up or residue on the upper regions of the web. Accordingly, the presence of regions 65 may be limited to the first surface of the web, and hence provide X-Y functionality, or limited to the interior of the fluid passageways, but is preferably employed to best advantage both on the first surface of the web and within the fluid passageways.

Accordingly, in nonwoven web structures of the present invention the surface energy gradients provide a synergistic effect in combination with the capillary nature of the structure to provide enhanced fluid transport and handling characteristics. Fluid on the first surface of the web encounters two differing, complementary driving forces in its journey away from the first surface and toward the second or opposing surface of the web, and typically further onward into the interior of the absorbent article. These two forces likewise combine to oppose fluid movement toward the first surface of the web, thus reducing the incidence of rewet and increasing the surface dryness of the web.

By way of a representative illustration of the synergism of the present invention vis-à-vis the combination or superposition of capillary and surface energy effects, nonwoven webs according to the present invention have been found to exhibit a unique combination of properties viewed as important from a consumer perspective. More particularly, capillary webs according to the present invention have been found to exhibit good acquisition, dryness, and masking characteristics, which will be defined hereafter.

In general, acquisition is a reflection of the degree to which the fluid transport web does or does not interfere with fluid pass-through. Improved acquisition rates/times reflect little interference or impedance of fluid pass-through, as well as actual influence of fluid driving forces such as capillarity and surface energy gradients. Dryness is a reflection of the degree to which the fluid transport structure resists fluid transport in the opposite direction, in essence, the degree to which the structure acts as a one-way valve for fluid flow in a preferential direction. Masking reflects the cleanliness of the surface after fluid pass-through, further defined as the degree of coloration remaining (with a colored fluid) as well as the size or extend of the discolored region.

Typically, as surface energy of a given capillary web structure decreases uniformly the masking and dryness at the surface improve, but at the expense of a reduction in acquisition characteristics. Conversely, improvements in acquisition realized by a uniform increase in surface energy of a given capillary web structure are typically offset by reduced masking and dryness characteristics. By utilizing the surface energy gradient principles of the present invention, wherein the surface energy of the upper surface is decreased while the surface energy of the lower surface remains higher, and particularly with the preferred orientation and location of the gradients themselves, increases in acquisition, dryness, and/or masking characteristics may be obtained without sacrifices in the remaining parameters.

Suitable analytical or test methods for determining web performance with regard to these attributes are described in greater detail in the ANALYTICAL METHODS section below.

A number of physical parameters should be considered in designing a web according to the present invention, more particularly with regard to appropriately sizing and positioning the surface energy gradients for proper fluid handling. Such factors include the magnitude of the surface energy differential (which depends upon the materials utilized), migratability of materials, bio-compatibility of materials, porosity or capillary size, overall web caliper and geometry, surface topography, fluid viscosity and surface tension, and the presence or absence of other structures on either side of the web.

Preferably, the regions 65 of the web 22 have a work of adhesion for water in the range of about 0 $erg/_{cm}2$ to about 150 $erg/_{cm}2$, more preferably in the range of about 0 $erg/_{cm}2$ to about 100 $erg/_{cm}2$, and most preferably in the range of about 0 $erg/_{cm}2$ to about 75 $erg/_{cm}2$. Preferably, the remainder of the web surrounding regions 65 has a work of adhesion for water in the range of about 0 $erg/_{cm}2$ to about 150 $erg/_{cm}2$, more preferably in the range of about 25 $erg/_{cm}2$ to about 150 $erg/_{cm}2$, and most preferably in the range of about 50 $erg/_{cm}2$ to about 150 $erg/_{cm}2$.

Preferably, the difference in the work of adhesion for water between the regions 65 and the remainder of the web is in the range of about 5 $erg/_{cm}2$ to about 145 $erg/_{cm}2$, more preferably in the range of about 25 $erg/_{cm}2$ to about 145 $erg/_{cm}2$, and most preferably in the range of about 50 $erg/_{cm}2$ to about 145 $erg/_{cm}2$.

A suitable surface treatment is a silicone release coating from Dow Corning of Midland, Mich. available as Syl-Off 7677 to which a crosslinker available as Syl-Off 7048 is added in proportions by weight of 100 parts to 10 parts, respectively. Another suitable surface treatment is a coating of a UV curable silicone comprising a blend of two silicones commercially available from General Electric Company, Silicone Products Division, of Waterford, N.Y., under the designations UV 9300 and UV 9380C-D1, in proportions by weight of 100 parts to 2.5 parts, respectively. The surface energy of the silicone release coating on the first surface of the nonwoven web is less than the surface energy of the individual fibers 60 forming the nonwoven web 22.

Other suitable treatment materials include, but are not limited to, fluorinated materials such as fluoropolymers (e.g., polytetrafluoroethylene (PTFE), commercially available under the trade name TEFLON®) and chlorofluoropolymers. Other materials which may prove suitable for providing regions of reduced surface energy include Petrolatum, latexes, paraffins, and the like, although silicone materials are presently preferred for use in webs in the absorbent article context for their biocompatibility properties. As used herein, the term "biocompatible" is used to refer to materials having a low level of specific adsorption for, or in other words a low affinity for, biospecies or biological materials such as gluco-proteins, blood platelets, and the like. As such, these materials tend to resist deposition of biological matter to a greater extent than other materials under in-use conditions. This property enables them to better retain their surface energy properties as needed for subsequent fluid handling situations. In the absence of biocompatibility, the deposition of such biological material tends to increase the roughness or non-uniformity of the surface, leading to increased drag force or resistance to fluid movement. Consequently, biocompatibility corresponds to reduced drag force or resistance to fluid movement, and hence faster access of fluid to the surface energy gradient and capillary structure. Maintenance of substantially the same surface energy also maintains the original surface energy differential for subsequent or enduring fluid depositions.

Biocompatibility, however, is not synonymous with low surface energy. Some materials, such as polyurethane, exhibit biocompatibility to some degree but also exhibit a comparatively high surface energy. Some low surface energy materials which might otherwise be attractive for use herein, such as polyethylene, lack biocompatibility. Presently preferred materials such as silicone and fluorinated materials advantageously exhibit both low surface energy and biocompatibility.

Suitable surfactants for hydrophilizing or increasing the surface energy of the selected regions of the web to have high surface energy include, for example, ethoxylated esters such as Pegosperse® 200-ML, manufactured by Glyco Chemical, Inc. of Greenwich, Conn., ATMER® 645, manufactured by ICI, glucose amides, tri-block copolymers of ethylene oxide and propylene oxide such as Plutonit® P103, manufactured by BASF, and copolymers of silicone and ethylene glycol such as DC190, manufactured by Dow Corning of Midland, Mich.

While much of the foregoing discussion has focused on the presently preferred approach of beginning with a predominantly hydrophilic web and applying a coating, treatment, or overlying layer of material to generate low surface energy regions and to render the upper portions hydrophobic, it is to be understood that other approaches to generating surface energy gradients are contemplated as well and are within the scope of the present invention. Such approaches would include applying a hydrophilic material (e.g., a hydrophilic latex) to the lower portions of an originally hydrophobic web to generate hydrophilic regions with boundaries at interfaces with hydrophobic web surfaces, forming the web of two or more materials of diverse surface energy characteristics with surface energy gradients formed by boundaries between the respective materials, forming the web of a material predominantly hydrophobic or predominantly hydrophilic and altering the surface chemistry of selected regions thereof by mechanical, electromagnetic, or chemical bombardment or treatment techniques know in the art to thus generate selective surface energy gradients, preferential migration of chemical web components capable of surface energy alteration, treating hydrophobic regions to be temporarily hydrophilic and reveal surface energy gradients in use, etc.

Figure 7:
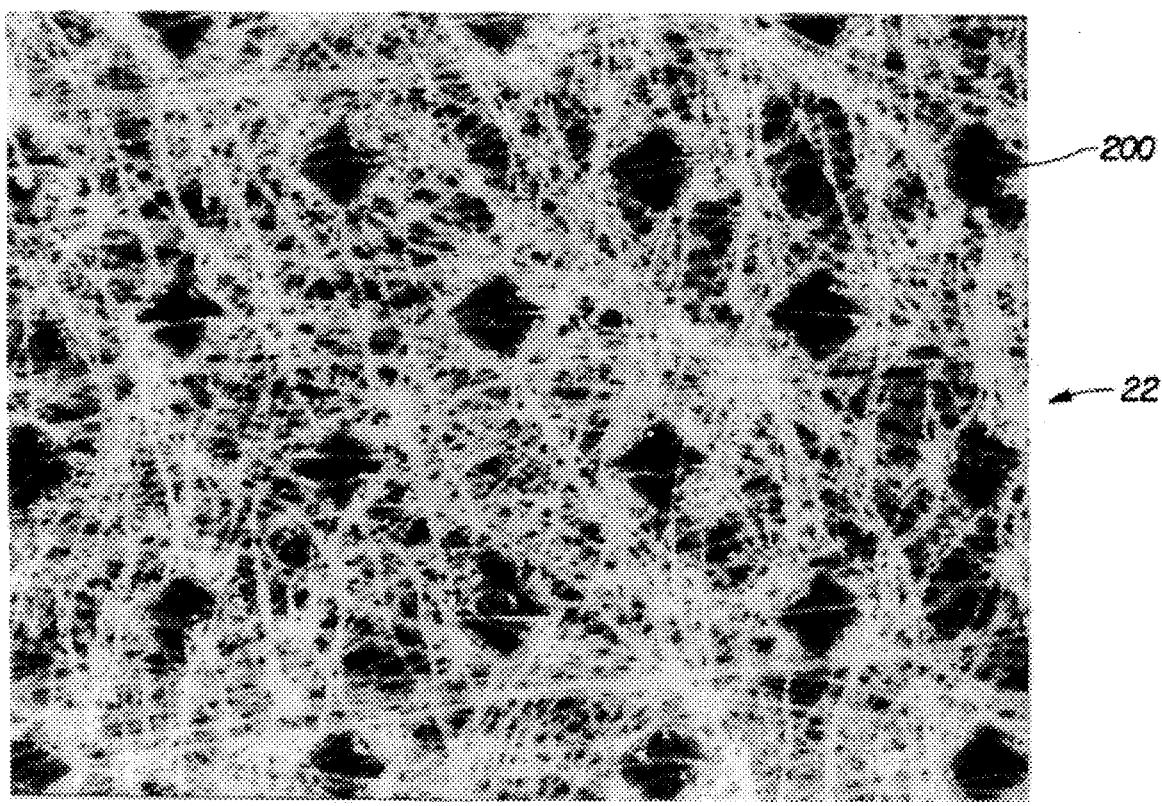
FIG. 7 is an enlarged plan view photograph of a nonwoven web prior to being weakened.

Referring now to FIG. 7, there is shown a photograph of a nonwoven web 22 prior to entering nip 70. As can be seen in FIG. 7, the coherent nonwoven web comprises a plurality of fibers joined together by point calendered bonds 200 to form a coherent web structure. The nonwoven web 22 shown in FIG. 7 does not have any surface treatment applied thereto.

Figure 8:
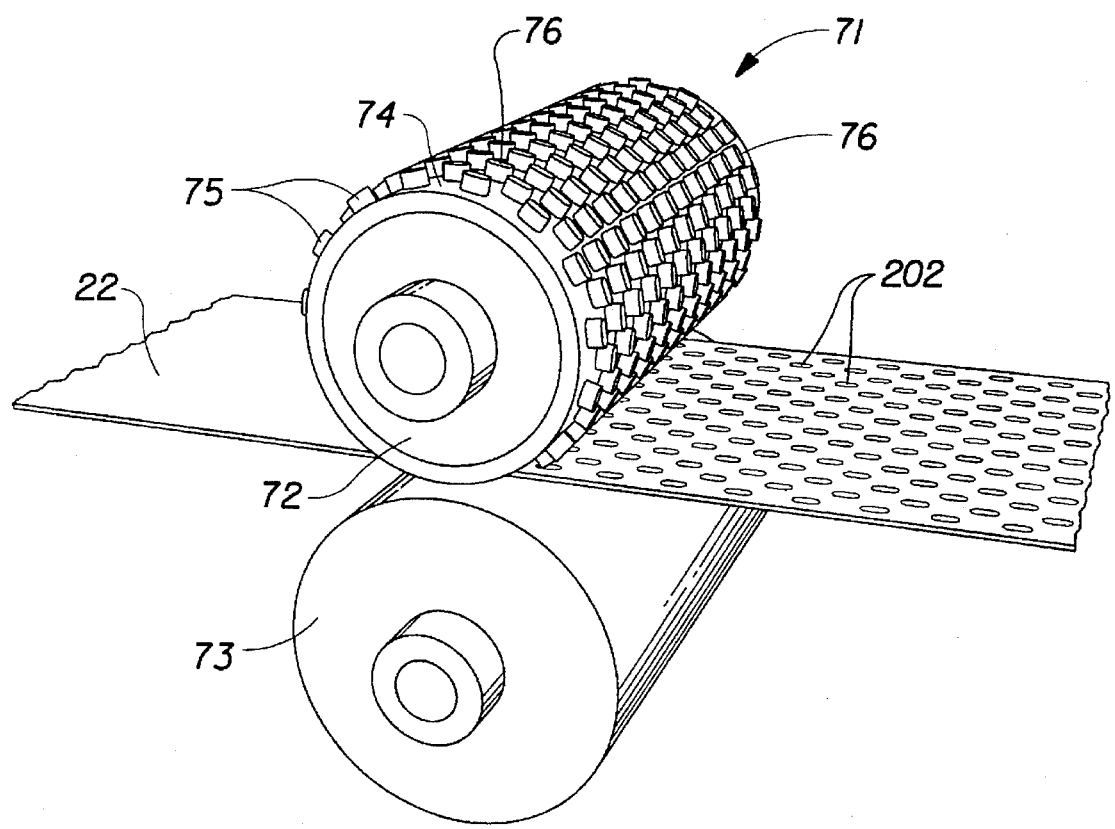
FIG. 8 is an enlarged perspective illustration of a web weakening arrangement of the present invention.

From the sprayer 26, the nonwoven web 22 passes through nip 70 of the web weakening arrangement 71 formed by rollers 72 and 73. Referring now to FIG. 8, the web weakening roller arrangement 71 preferably comprises a patterned calendar roller 72 and a smooth anvil roller 73. One or both of the patterned calendar roller and the smooth anvil roller may be heated and the pressure between the two rollers may be adjusted by well known means to provide the desired temperature, if any, and pressure to concurrently weaken and melt-stabilize the nonwoven web at a plurality of locations.

The patterned calendar roller 72 is configured to have a circular cylindrical surface 74, and a plurality of protuberances or pattern elements 75 which extend outwardly from surface 74. The protuberances 75 are disposed in a predetermined pattern with each protuberance 75 being configured and disposed to precipitate a weakened, melt-stabilized location in the nonwoven web 22 to effect a predetermined pattern of weakened, melt-stabilized locations in the nonwoven web. As shown in FIG. 8, patterned calendar roller 72 has a repeating pattern of protuberances 75 which extend about the entire circumference of surface 74. Alternatively, the protuberances 75 may extend around a portion, or portions or the circumference of surface 74.

The protuberances 75 are preferably truncated conical shapes which extend radially outwardly from surface 74 and which have elliptical distal end surfaces 76. Although it is not intended to thereby limit the scope of the present invention to protuberances of only this configuration. Other suitable shapes for distal ends 76 include, but are not limited to circular, square, rectangular, etc. The roller 72 is finished so that all of the end surfaces 76 lie in an imaginary right circular cylinder which is coaxial with respect to the axis of rotation of roller 72.

The protuberances 75 are disposed in a regular predetermined pattern of rows and columns in the embodiment shown in FIG. 8, although it is not intended to thereby limit the scope of the present invention to the pattern of protuberances of only this configuration. The protuberances may be disposed in any predetermined pattern about patterned calendar roll 72.

Anvil roller 73, is preferably a smooth surfaced, right circular cylinder of steel.

Figure 9:
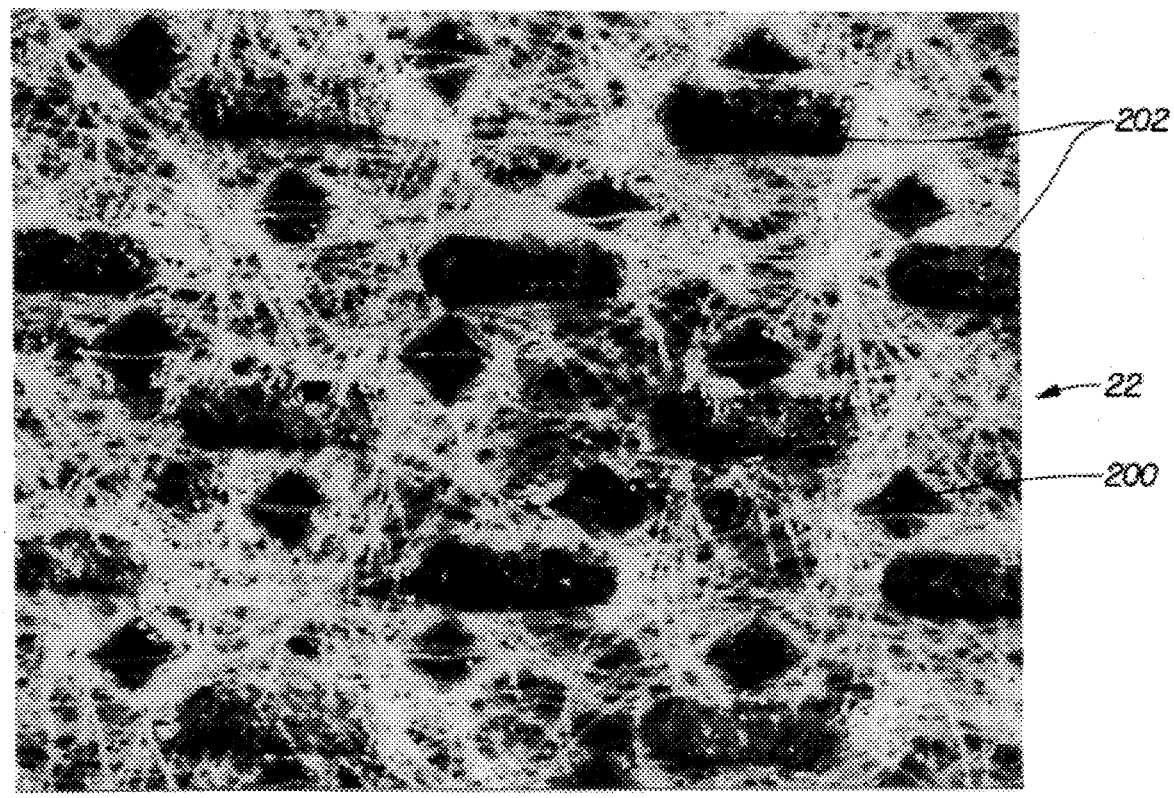
FIG. 9 is an enlarged plan view photograph of a nonwoven web after the nonwoven web has been weakened at a plurality of locations.

FIG. 9 is a photograph of the nonwoven web 22 after having passed through the weakening roller arrangement 71, and prior to passing through the nip 80 of the incremental stretching system 82. As can be seen in the photograph, the nonwoven web 22 includes a plurality of weakened, melt-stabilized locations 202. Weakened, melt-stabilized locations 202 generally correspond to the pattern of protuberances 75 extending from the surface 74 of patterned calendar roller 72. As seen in FIG. 9; the nonwoven web 22 also includes coherent web forming point calendered bonds 200 which serve to maintain the structural integrity of the nonwoven web.

From the weakening roller arrangement 71, the nonwoven web 22 passes through nip 80 formed by the incremental stretching system 82 employing opposed pressure applicators having three-dimensional surfaces which at least to a degree are complimentary to one another.

Figure 10:
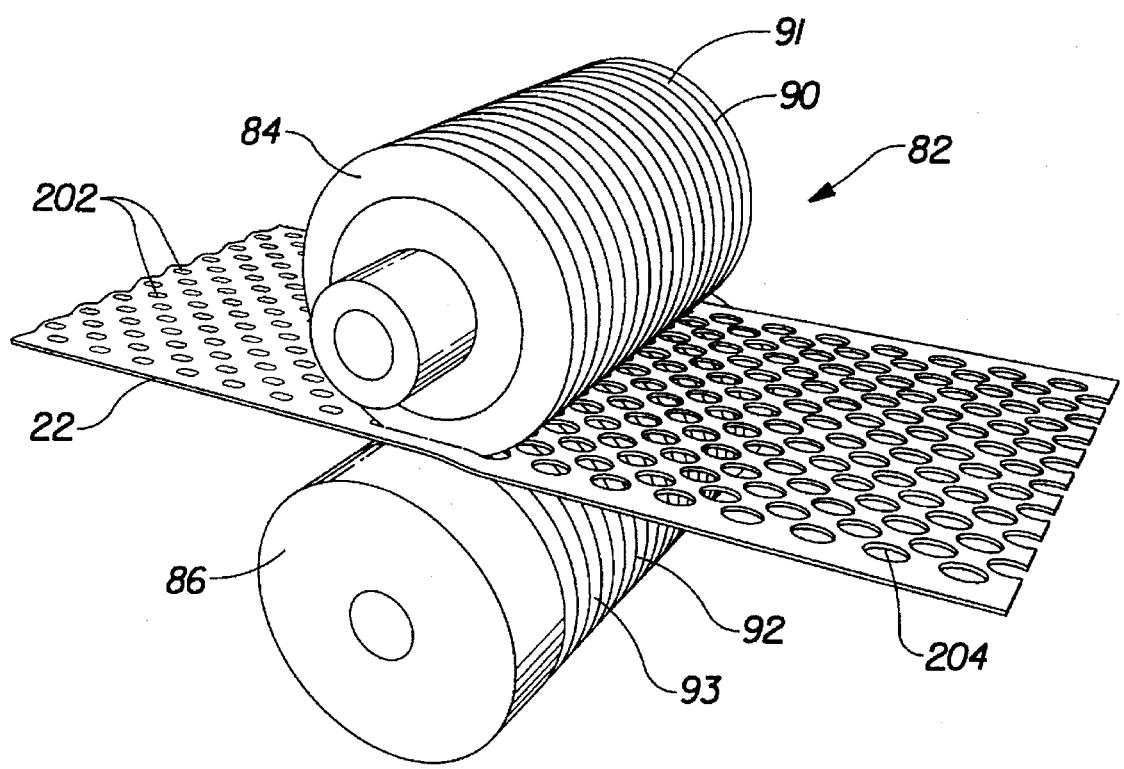
FIG. 10 is an enlarged perspective illustration of an incremental stretching system of the present invention.

Referring now to FIG. 10, there is shown a fragmentary enlarged view of the incremental stretching system 82 comprising incremental stretching rollers 84 and 86. The incremental stretching roller 84 includes a plurality of teeth 90 and corresponding grooves 91 which extend about the entire circumference of roller 84. Incremental stretching roller 86 includes a plurality of teeth 92 and a plurality of corresponding grooves 93 which extend about the entire circumference of roller 86. The teeth 90 on roller 84 intermesh with or engage the grooves 93 on roller 86, while the teeth 92 on roller 86 intermesh with or engage the grooves 91 on roller 84. As the nonwoven web 22 having weakened, melt-stabilized locations 202 passes through the incremental stretching system 82 the nonwoven web 22 is subjected to incremental stretching or tensioning in the CD or cross-machine direction causing the nonwoven web 22 to be extended in the CD direction. Alternatively or additionally, the nonwoven web 22 may be subjected to incremental stretching or tensioning in the MD or machine direction causing the nonwoven web 22 to be extended in the MD direction. The tensioning force placed on the nonwoven web 22 is preferably adjusted such that it causes the weakened, melt-stabilized locations 22 to rupture creating a plurality of apertures 204 coincident with the weakened melt-stabilized locations 202 in the nonwoven web 22. However, the bonds of the nonwoven web 22 are preferably strong enough such that they do not rupture during tensioning, thereby maintaining the nonwoven web in a coherent condition even as the weakened, melt-stabilized locations rupture. However, it may be desirable to have some of the bonds rupture during tensioning.

Other exemplary structures of incremental stretching mechanisms including incremental stretching rollers suitable for incrementally stretching the nonwoven web 22 are described in International Patent Publication No. WO 95/03765, published Feb. 9, 1995, in the name of Chappell, et al., the disclosure of which is incorporated herein by reference.

Figure 11:
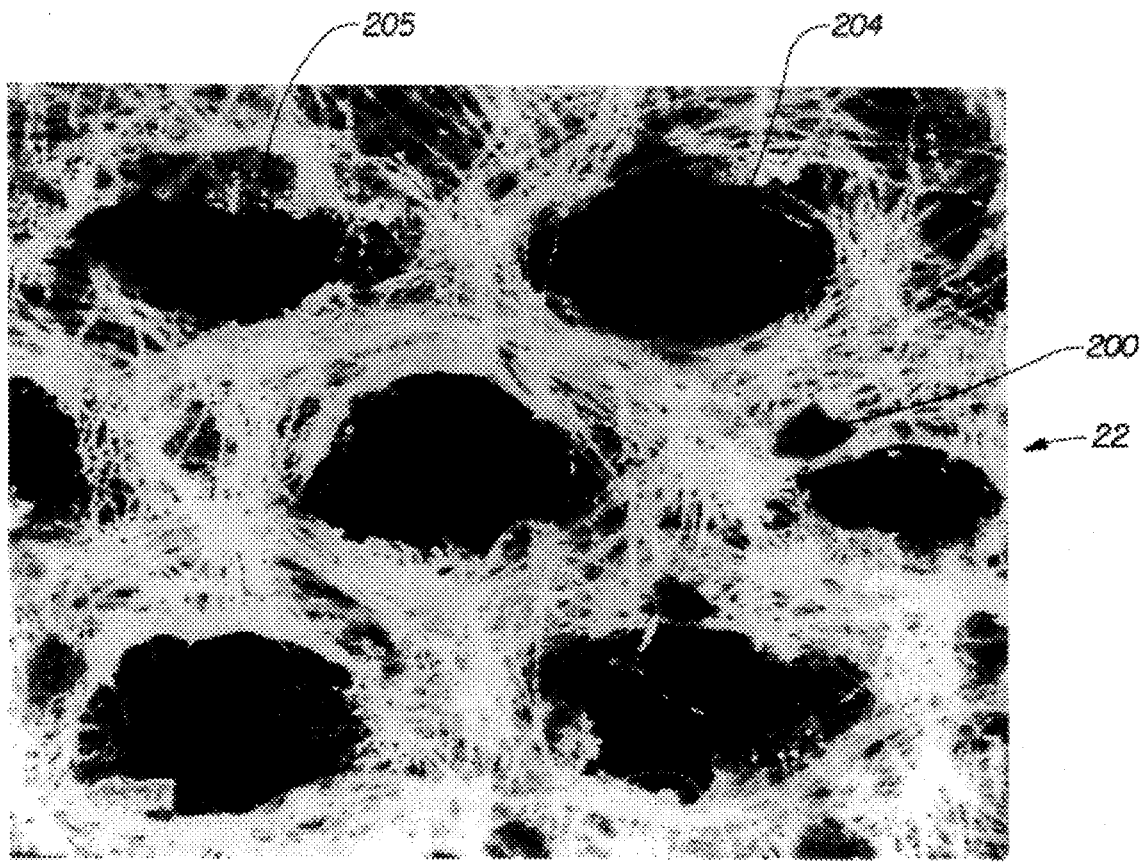
FIG. 11 is an enlarged plan view photograph of a nonwoven web after tension has been applied to rupture the nonwoven web at the weakened locations to create aperture in the nonwoven web.

Referring now to FIG. 11, there is shown a photograph of the nonwoven web 22 after having been subjected to the tensioning force applied by the incremental stretching system 82. As can be seen in the photograph, the nonwoven web 22 now includes a plurality of apertures 204 which are coincident with the weakened, melt-stabilized locations 202 of the nonwoven web shown in FIG. 9. A portion of the circumferential edges of the apertures 204 comprise remnants 205 of the melt-stabilized locations 202.

The nonwoven web 22 is preferably taken up on wind-up roll 50 and stored. Alternatively, the nonwoven web 22 may be fed directly to a production line where it is used to form a topsheet on a disposable absorbent article.

Figure 12:
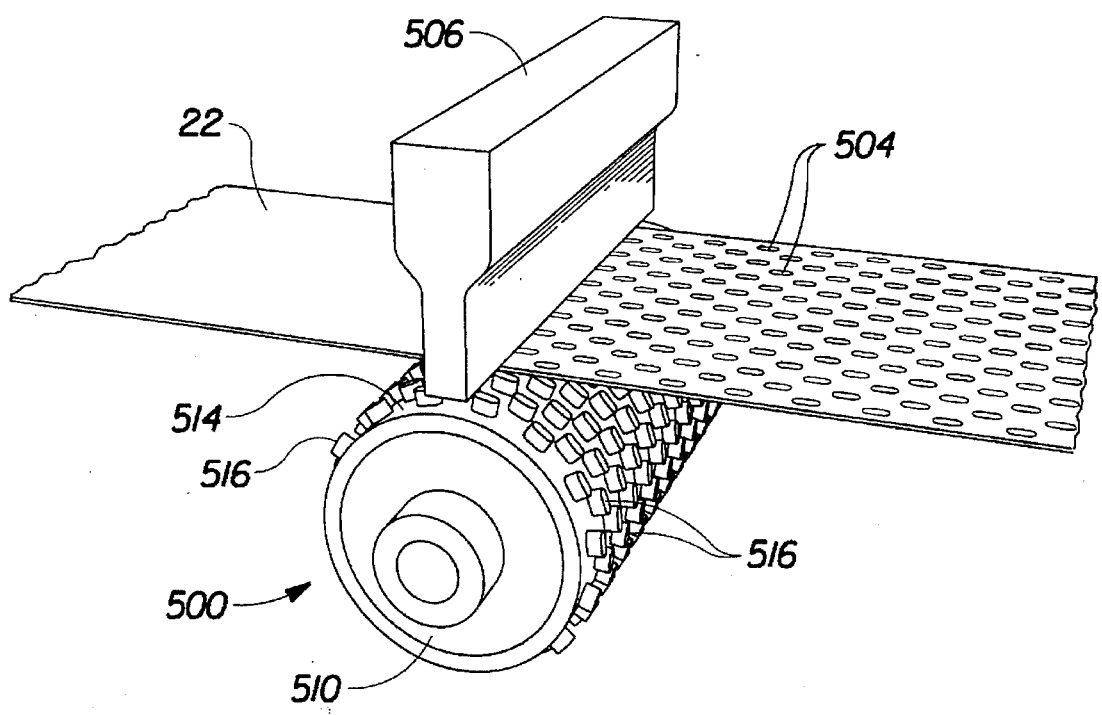
FIG. 12 is an enlarged perspective illustration of another web weakening arrangement of the present invention.

Referring now to FIG. 12, there is shown another web weakening arrangement 500 preferably comprising an ultrasonic transducer 506 and a cylinder 510. As the nonwoven web 22 is forwarded between the ultrasonic transducer 506 and the anvil cylinder 510, the nonwoven web 22 is subjected to ultrasonic vibrational energy whereupon predetermined pattern locations of the nonwoven web 22 are weakened and melt-stabilized. Anvil 510 has a multiplicity of discrete pattern protuberances which are generally designated 516 disposed on its outwardly facing surface 514 in a predetermined pattern which extends about the entire circumference of the anvil cylinder. The protuberances 516 are disposed in a predetermined pattern with each protuberance 516 being configured and disposed to precipitate a weakened, melt-stabilized location 504 in the nonwoven web 22 to effect a predetermined pattern of weakened, melt-stabilized locations in the nonwoven web 22. As shown in FIG. 12, anvil 510 has a repeating pattern of protuberances 516 which extend about the entire circumference of surface 514. Alternatively, the protuberances 516 may extend around a portion, or portions of the circumference of surface 514.

REPRESENTATIVE ABSORBENT ARTICLE

As used herein, the term "absorbent article" refers generally to devices used to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinent pads, and the like, as well as bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

Figure 13:
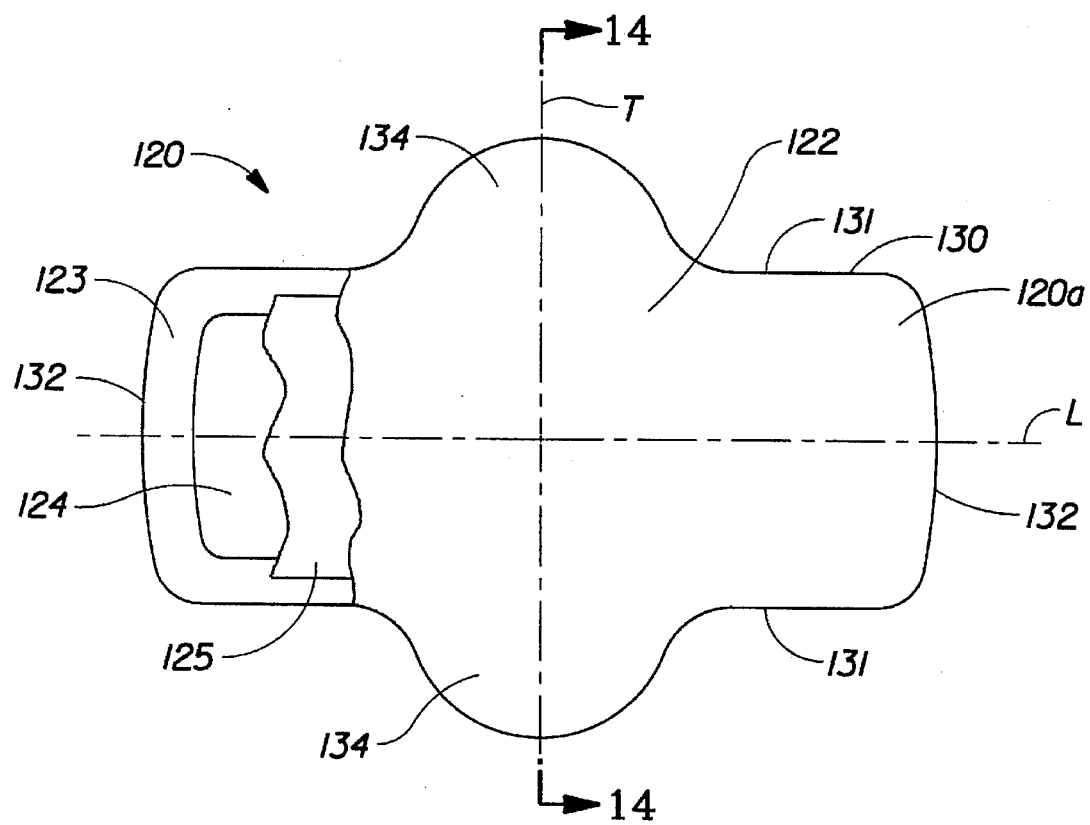
FIG. 13 is a top plan view of a sanitary napkin with portions of the sanitary napkin cut away to more clearly show the construction of the sanitary napkin.

A preferred embodiment of a unitary disposable absorbent article made in accordance herewith is the catamenial pad, sanitary napkin 120, shown in FIG. 13. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, and the like, as well as other webs designed to facilitate fluid transport away from a surface such as disposable towels, facial tissues, and the like.

It is to be understood that the overall size, shape, and/or configuration of the absorbent article, if any, into which fluid transport webs according to the present invention are incorporated, or utilized in conjunction with, have no criticality or functional relationship to the principles of the present invention. Such parameters, however, must be considered along with the intended fluid and intended functionality when determining appropriate web configurations and appropriate orientation of surface energy gradients according to the present invention.

Sanitary napkin 120 is illustrated as having two surfaces such as first surface 120a, sometimes referred to as a wearer-contacting or facing surface, a body-contacting or facing surface or "body surface", and second surface 120b, sometimes referred to as a garment-facing or contacting surface, or "garment surface". The sanitary napkin 120 is shown in FIG. 13 as viewed from its first surface 120a. The first surface 120a is intended to be worn adjacent to the body of the wearer. The second surface 120b of the sanitary napkin 120 (shown in FIG. 14) is on the opposite side and is intended to be placed adjacent to the wearer's undergarment when the sanitary napkin 120 is worn.

The sanitary napkin 120 has two centerlines, a longitudinal centerline "L" and a transverse centerline "T". The term "longitudinal", as used herein, refers to a line, axis or direction in the plane of the sanitary napkin 120 that is generally aligned with (e.g., approximately parallel to) a vertical plane which bisects a standing wearer into leer and right body halves when the sanitary napkin 120 is worn. The terms "transverse" or "lateral" as used herein, are interchangeable and refer to a line, axis or direction which lies within the plane of the sanitary napkin 120 that it generally perpendicular to the longitudinal direction. FIG. 13 also shows that the sanitary napkin 120 has a periphery 130 which is defined by the outer edges of the sanitary napkin 120 in which the longitudinal edges (or "side edges") are designated 131 and the end edges (or "ends") are designated 132.

FIG. 13 is top plan view of a sanitary napkin 120 of the present invention in a substantially flat state with portions of the sanitary napkin being cut away to more clearly show the construction of the sanitary napkin 120 and with the portion of the sanitary napkin 120 which faces or contacts the wearer 120a oriented towards the viewer. As shown in FIG. 13, the sanitary napkin 120 preferably comprises a liquid pervious topsheet 122, a liquid impervious backsheet 123 joined with the topsheet 122, an absorbent core 124 positioned between the topsheet 122 and the backsheet 123, and a secondary topsheet or acquisition layer 125 positioned between the top sheet 122 and the absorbent core 124.

The sanitary napkin 120 preferably includes optional side flaps or "wings" 134 that are folded around the crotch portion of the wearer's panty. The side flaps 134 can serve a number of purposes, including, but not limited to helping to hold the napkin in proper position while protecting the wearer's panty from soiling and keeping the sanitary napkin secured to the wearer's panty.

Figure 14:
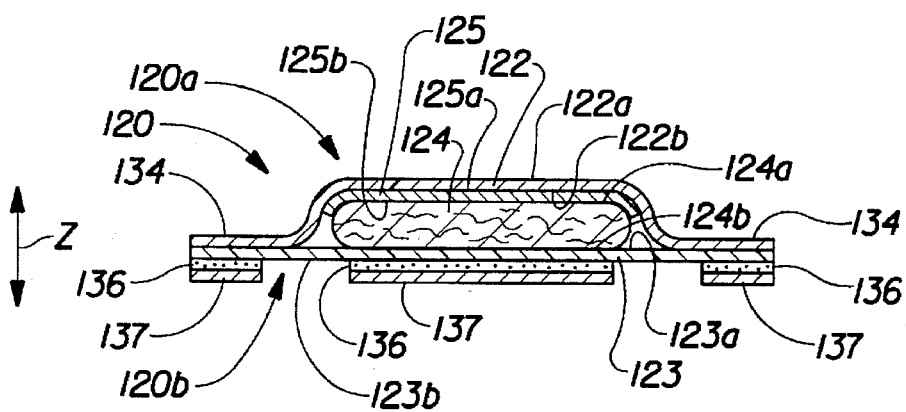
FIG. 14 is a cross-sectional view of the sanitary napkin of FIG. 13 taken along section line 14—14.

FIG. 14 is a cross-sectional view of the sanitary napkin 120 taken along section line 14—14 of FIG. 13. As can be seen in FIG. 14, the sanitary napkin 120 preferably includes an adhesive fastening means 136 for attaching the sanitary napkin 120 to the undergarment of the wearer. Removable release liners 137 cover the adhesive fastening means 136 to keep the adhesive from sticking to a surface other than the crotch portion of the undergarment prior to use.

The topsheet 122 has a first surface 122a and a second surface 122b positioned adjacent to and preferably secured to a first surface 125a of the fluid acquisition layer 125 to promote fluid transport from the topsheet to the acquisition layer. The second surface 125b of the acquisition layer 125 is positioned adjacent to and is preferably secured to the first surface 124a of an absorbent core or fluid storage layer 124 to promote fluid transport from the acquisition layer to the absorbent core. The second surface 124b of the absorbent core 124 is positioned adjacent to and is preferably secured to the first surface 123a of the backsheet 123.

In addition to having a longitudinal direction and a transverse direction, the sanitary napkin 120 also has a "Z" direction or axis, which is the direction proceeding downwardly through the topsheet 122 and into whatever fluid storage layer or core 124 that may be provided. The objective is to provide a substantially continuous path between the topsheet 122 and the underlying layer or layers of the absorbent article herein, such that fluid is drawn in the "Z" direction and away from the topsheet of the article and toward its ultimate storage layer.

The absorbent core 124 may be any absorbent means which is capable of absorbing or retaining liquids (e.g., menses and/or urine). As shown in FIGS. 13 and 14, the absorbent core 124 has a body surface 124a, a garment facing surface 124b side edges, and end edges. The absorbent core 124 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied as (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, the Procter & Gamble Company, published Oct. 22, 1986 in the name Duenk, et at. The disclosures of each of these patents are incorporated herein by reference.

A preferred embodiment of the absorbent core 124 has a surface energy gradient similar to the surface energy gradient of the topsheet 122. The body facing surface 124a of the absorbent core and the portion of the absorbent core 124 immediately adjacent the body facing surface 124a preferably has a relatively low surface energy as compared to the garment facing surface 124b which has a relatively high surface energy. It is important to note that while there is a surface energy gradient within the absorbent core 124, the surface energy of the wearer-contacting or the body facing surface 124a of the absorbent core is preferably greater than the surface energy of the garment facing surface 125b of the acquisition layer 125. This relationship is preferred in order that fluid may be pulled or driven from the acquisition layer into the absorbent core. If the surface energy of the body facing surface 124a of the absorbent core were less than that of the garment facing surface 125b of the acquisition layer fluid in the acquisition layer 125 would be repelled by the absorbent core, thus rendering the absorbent core useless.

The backsheet 123 and the topsheet 122 are positioned adjacent the garment facing surface and the body facing surface respectively of the absorbent core 124 and are preferably joined thereto and to each other by attachment means (not shown) such as those well known in the art. For example, the backsheet 123 and/or the topsheet 122 may be secured to the absorbent core or to each other by a uniform continuous layer of adhesive, a patterned layer of adhesive or any array of separate lines, spirals or spots of adhesive. Adhesives which have been found to be satisfactory are manufactured by H. B. Fuller Company of St. Paul, Minn. under the designation HL-1258, and by Findlay of Minneapolis, Minn., under the designation H-2031. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may comprise heat bonds, pressure bonds, ultrasonic bonds, dynamic mechanical bonds or any other suitable attachment means or combinations of these attachment means as are known in the art.

The backsheet 123 is impervious to liquids (e.g., menses and/or urine) and is preferably manufactured from a thin plastic film, although other flexible liquid impervious materials may also be used. As used herein, the term "flexible" refers to materials which are compliant and are more readily conformed to the general shape and contours of the human body. The backsheet 123 prevents the exudates absorbed and contained in the absorbent core from wetting articles which contact the sanitary napkin 20 such as pants, pajamas and undergarments. The backsheet 123 may thus comprise a woven or nonwoven material, polymeric films such as thermoplastic films of polyethylene or polypropylene, or composite materials such as a film-coated nonwoven material. Preferably, the backsheet of the polyethylene film having a thickness of from about 0.012 mm (0.5 mil) to about 0.051 mm (2.0 mil). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 123 may permit vapors to escape from the absorbent core 124 (i.e., breathable) while still preventing exudates from passing through the backsheet 123.

In use, the sanitary napkin 120 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 123b of the backsheet 123 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 137 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 120 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 134 each of which are adjacent to and extend laterally from the side edge of the absorbent core. The flaps 134 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 125 may be positioned between the topsheet 122 and the absorbent core 124. The acquisition layer 125 may serve several functions including improving wicking of exudates over and into the absorbent core. There are several reasons why the improved wicking of exudates is important, including providing a more even distribution of the exudates throughout the absorbent core and allowing the sanitary napkin 120 to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al., and now abandoned. The disclosures of each of these references are hereby incorporated herein by reference. In a preferred embodiment, the acquisition layer may be joined with the topsheet by any of the conventional means for joining webs together, most preferably by fusion bonds as is more fully described in the above-referenced Cree application.

In a preferred embodiment the acquisition layer 125 preferably has a surface energy gradient similar to that of the topsheet 122 and/or absorbent core 124. In a preferred embodiment, the first or wearer-facing surface 125a preferably has a relatively low surface energy as compared to the absorbent pad contacting surface 125b. Preferably, the surface energy of the first surface 125a of the acquisition layer 125 is preferably greater than the surface energy of the second surface of the topsheet 122. Furthermore, the second surface of the acquisition layer 125b has a relatively low surface energy compared to the surface energy of the body facing surface 124a of the absorbent core 124.

Figure 15:
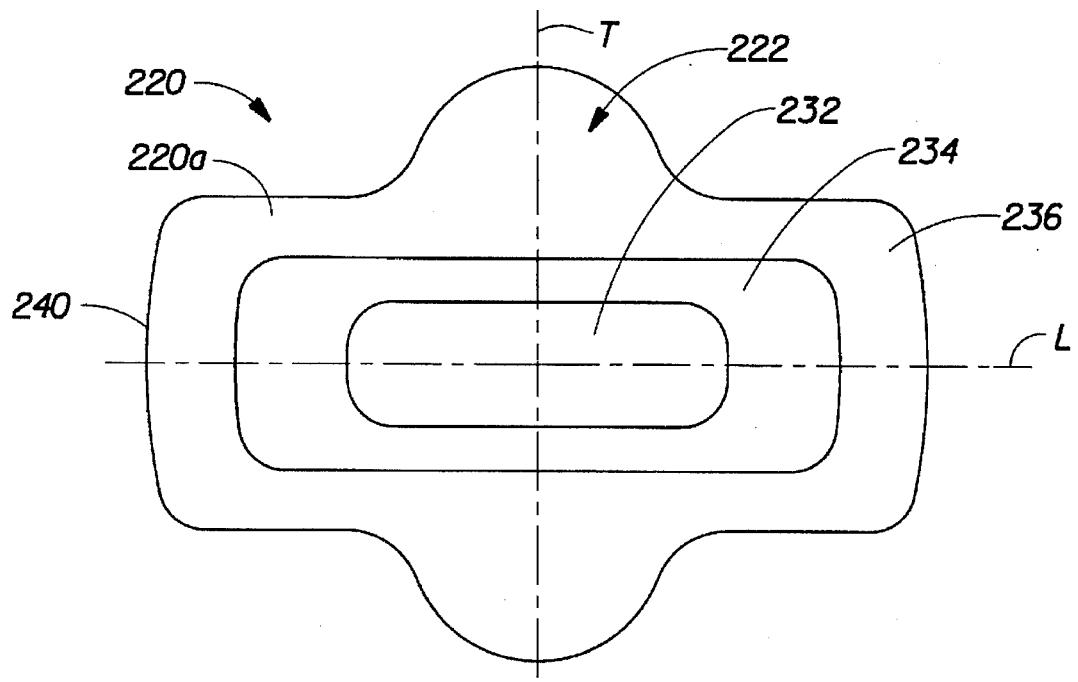
FIG. 15 is a top plan view of the topsheet portion of a sanitary napkin embodiment made according to the present invention.

Referring now to FIG. 15 there is shown another preferred embodiment of a sanitary napkin 220 made according to the present invention. The sanitary napkin 220 is shown in FIG. 15 as viewed from its first or wearer-contacting surface 220a. The sanitary napkin 220 includes a liquid pervious topsheet 222, a liquid impervious backsheet (not shown), joined with the topsheet 222, an absorbent core (not shown), positioned between the topsheet 222 and the backsheet, and an acquisition layer (not shown) positioned between the topsheet 222 and the absorbent core.

The topsheet 222 preferably includes a plurality of regions and/or zones, such as a first central region 232, a second region 234 adjacent to and contiguous with the first region 232, and a third region 236 adjacent to and contiguous with the second region 234. Preferably, the first surface of the topsheet 222 within the first central region 232 has a relatively higher surface energy than that of the topsheet 222 within the adjacent second region 234. Likewise, the first surface of the topsheet 222 within the second region 234 has a relatively higher surface energy than that of the topsheet 222 within the adjacent third region 236. Thus, fluid deposited on the topsheet 122 will be driven from the third region 236 toward the second region 234 and from the second region 234 toward the first region 232. Accordingly, fluid will be directed from the third region 236 towards the first region 232 of the topsheet 222 to help prevent any run-off of fluids over the periphery 240 of the sanitary napkin.

While the first or wearer-contacting surface of the topsheet 222 has a surface energy gradient from region to region, which may be discrete or continuous, the topsheet 222 will also preferably have an additional surface energy gradient between the first surface and the intermediate portions of the topsheet 222. The surface energy of the intermediate portions 234 within the respective regions of the topsheet, will be higher than the surface energy of the wearer-contacting surface in the first, second and third regions of the topsheet 222. Thus, the topsheet will also promote the transmission of fluids in the "Z" direction similar to that of web 22 disclosed in FIG. 3.

In some situations it may be desirable to have a surface energy gradient on the first surface of the topsheet 222 which forces fluid from the first region to the second region, and from the second region to the third region. In such an embodiment, the first surface of the topsheet 222 within the first region 232 has a relatively lower surface energy than that of the topsheet 222 within the adjacent second region 234. Similarly, the first surface of the topsheet 222 within the second region 234 has a relatively lower surface energy than that of the topsheet 222 within the adjacent third region 236. Thus, fluid deposited on the topsheet 222 will be driven from the first region 232 toward the second region 234, and from the second region 234 toward the third region 236. This type of surface energy gradient may be desirable when trying to fully utilize the absorbent capacity of the underlying absorbent core by spreading bodily fluids across the first surface of the topsheet, the fluids will have a more direct path to the peripheral portions of the underlying absorbent core.

The regions or zones 232, 234, 236 are shown in FIG. 15 as generally being of an oval configuration. However, the regions may be formed in a wide variety of shapes and sizes, such as rectangular, elliptical, hourglass, dogbone, asymmetric, triangular, circular, etc., or even random shapes and sizes.

Figure 16:
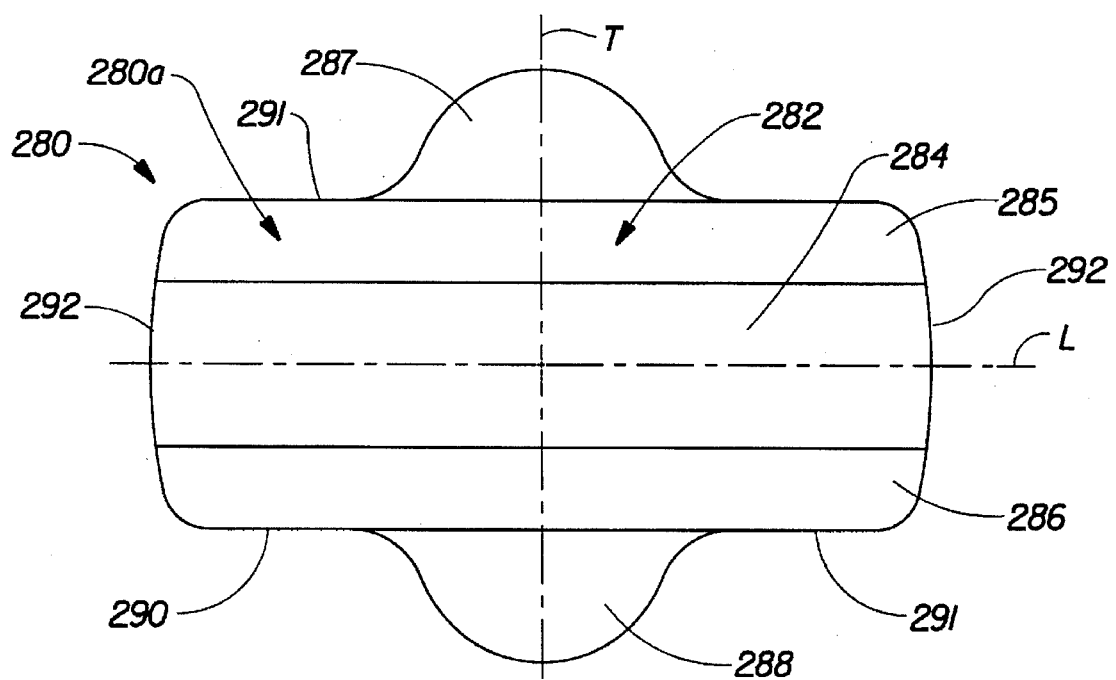
FIG. 16 is a top plan view of the topsheet portion of another sanitary napkin embodiment made according to the present invention.

Referring now to FIG. 16 there is shown a sanitary napkin 280 as viewed from its first surface 280a. The sanitary napkin 280 includes elements or components similar to that of sanitary napkin 120 shown in FIGS. 13 and 14 such as a liquid pervious topsheet 282, a liquid impervious backsheet joined with the topsheet 282, an absorbent core positioned between the topsheet 282 and the backsheet, and a secondary topsheet or acquisition layer positioned between the topsheet 282 and the absorbent core. The sanitary napkin 280 has a periphery 290 which is defined by the outer edges of the sanitary napkin 280 in which the longitudinal edges (or "side edges") are designated 291 and the end edges (or "ends") are designated 292.

The topsheet 282 includes a plurality of regions extending generally parallel to the longitudinal axis "L" of the sanitary napkin 280, and includes a first or central region 284 extending parallel to the longitudinal axis from one end of the sanitary napkin to the other end. Adjacent to the first or central region 284 is a pair of second regions 285, 286 extending essentially parallel to the first region 284. Adjacent the second regions 285, 286, respectively, are a pair of third regions 287, 288. Preferably, the first region has a relatively high surface energy as compared to the second regions 285, 286. Similarly, the second regions 285, 286 have a relatively high surface energy as compared to the third regions 287, 288.

Alternatively, the first region may have a relatively low surface energy as compared to the second regions 285, 286. The second regions 285, 286 may then have a relatively low surface energy as compared to the third regions 287, 288.

It should be noted that the surface energy characteristics of the regions depicted in FIGS. 15 and 16 are in addition to the surface energy gradients and characteristics of the present invention. Accordingly, within one or more of the defined regions in FIGS. 15 and 16 the surface energy features and characteristics described in FIG. 3 are included therein as well.

Figure 17:
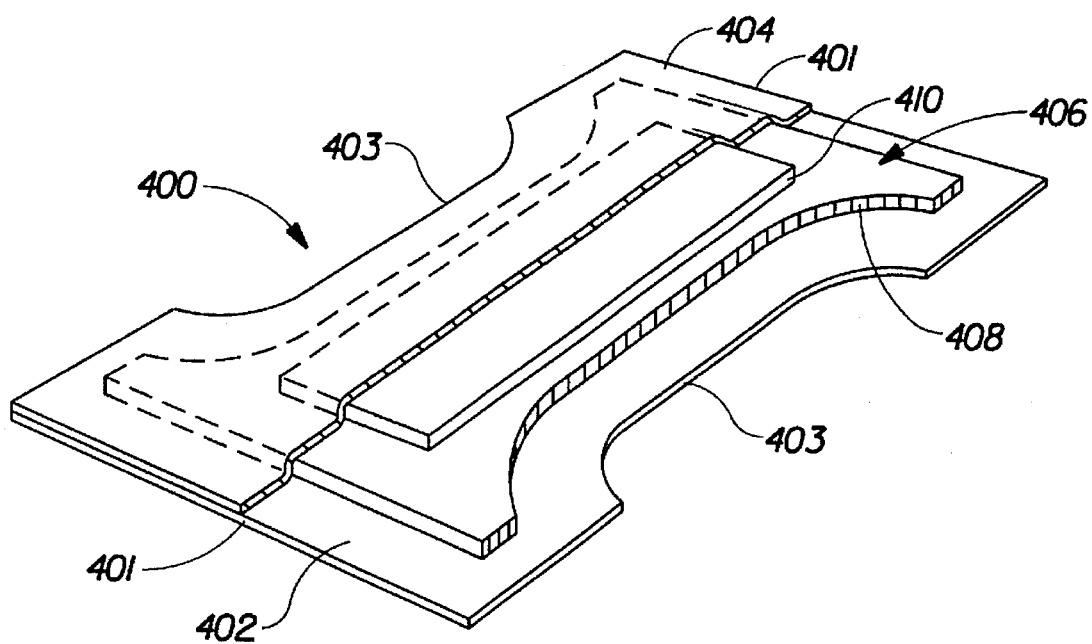
FIG. 17 is an enlarged, partially segmented, perspective illustration of a representative absorbent article in the form of a diaper made in accordance with the present invention.

A representative embodiment of a disposable absorbent article in the form of a diaper 400, is shown in FIG. 17. As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, sanitary napkins, facial tissues, paper towels, and the like. The diaper 400 depicted in FIG. 17 is a simplified absorbent article that could represent a diaper prior to its being placed on a wearer. It should be understood, however, that the present invention is not limited to the particular type or configuration of diaper shown in FIG. 17.

FIG. 17 is a perspective view of the diaper 400 in its uncontracted state (i.e., with all the elastic induced contraction removed) with portions of the structure being cut-away to more clearly show the construction of the diaper 400. The portion of the diaper 400 which contacts the wearer faces the viewer. The diaper 400 is shown in FIG. 17 to preferably comprise a liquid pervious topsheet 404; a liquid impervious backsheet 402 joined with the topsheet 404; and an absorbent core 406 positioned between the topsheet 404 and the backsheet 402. Additional structural features such as elastic members and fastening means for securing the diaper in place upon a wearer (such as tape tab fasteners) may also be included.

While the topsheet 404, the backsheet 402, and the absorbent core 406 can be assembled in a variety of well known configurations, a preferred diaper configuration is described generally in U.S. Pat. No. 3,860,003 (Buell), issued Jan. 14, 1975, the disclosure of which is incorporated by reference. Alternatively preferred configurations for disposable diapers herein are also disclosed in U.S. Pat. No. 4,808,178 (Aziz et al), issued Feb. 28, 1989; U.S. Pat. No. 4,695,278 (Lawson), issued Sep. 22, 1987; and U.S. Pat. No. 4,816,025 (Foreman), issued Mar. 28, 1989, the disclosures of each of these patents hereby being incorporated herein by reference.

FIG. 17 shows a preferred embodiment of the diaper 400 in which the topsheet 404 and the backsheet 402 are co-extensive and have length and width dimensions generally larger than those of the absorbent core 406. The topsheet 404 is joined with and superimposed on the backsheet 402 thereby forming the periphery of the diaper 400. The periphery defines the outer perimeter or the edges of the diaper 400. The periphery comprises the end edges 401 and the longitudinal edges 403.

The topsheet 404 is compliant, soft feeling, and non-irritating to the wearer's skin. Further, the topsheet 404 is liquid pervious permitting liquids to readily penetrate through its thickness. A suitable top sheet 404 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet 404 is made in accordance with the present invention and includes surface energy gradients therein.

A particularly preferred topsheet 404 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 404. For example, the topsheet 404 can be woven, nonwoven, spunbonded, carded, or the like. A preferred topsheet is carded, and thermally bonded by means well known to those skilled in the fabrics art. Preferably, the topsheet 404 has a weight from about 18 to about 25 grams per square meter, a minimum dry tensile strength of at least about 400 grams per centimeter in the machine direction, and a wet tensile strength of at least about 55 grams per centimeter in the cross-machine direction.

The backsheet 402 is impervious to liquids and is preferably manufactured from a thin plastic film, although other flexible liquid impervious materials may also be used. The backsheet 402 prevents the exudates absorbed and contained in the absorbent core 406 from wetting articles which contact the diaper 400 such as bed sheets and undergarments. Preferably, the backsheet 402 is polyethylene film having a thickness from about 0.012 mm (0.5 mil to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 402 is preferably embossed and/or matte finished to provide a more clothlike appearance. Further, the backsheet 402 may permit vapors to escape from the absorbent core 406 while still preventing exudates from passing through the backsheet 402.

The size of the backsheet 402 is dictated by the size of the absorbent core 406 and the exact diaper design selected. In a preferred embodiment, the backsheet 402 has a modified hourglass-shape extending beyond the absorbent core 406 a minimum distance of at least about 1.3 centimeters to about 2.5 centimeters (about 0.5 to about 1.0 inch) around the entire diaper periphery.

The topsheet 404 and the backsheet 402 are joined together in any suitable manner. As used herein, the term "joined" encompasses configurations whereby the topsheet 404 is directly joined to the backsheet 402 by affixing the topsheet 404 directly to the backsheet 402, and configurations whereby the topsheet 404 is indirectly joined to the backsheet 402 by affixing the topsheet 404 to intermediate members which in turn are affixed to the backsheet 402. In a preferred embodiment, the topsheet 404 and the backsheet 402 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 404 to the backsheet 402.

Tape tab fasteners (not shown for clarity) are typically applied to the back waistband region of the diaper 402 to provide a fastening means for holding the diaper on the wearer. The tape tab fasteners can be any of those well known in the art, such as the fastening tape disclosed in U.S. Pat. No. 3,848,594 (Buell), issued Nov. 19, 1974, the disclosure of which is hereby incorporated by reference. These tape tab fasteners or other diaper fastening means are typically applied near the corners of the diaper 400.

Elastic members (also not shown for clarity) are disposed adjacent the periphery of the diaper 400, preferably along each longitudinal edge 403, so that the elastic members tend to draw and hold the diaper 400 against the legs of the wearer. Alternatively, the elastic members can be disposed adjacent either or both of the end edges 401 of the diaper 400 to provide a waistband as well as or rather than leg cuffs. For example, a suitable waistband is disclosed in U.S. Pat. No. 4,515,595 (Kievit et al), issued May 7, 1985, the disclosure of which is hereby incorporated by reference. In addition, a method and apparatus suitable for manufacturing a disposable diaper having elastically contractible elastic members is described in U.S. Pat. No. 4,081,301 (Buell), issued Mar. 28, 1978, the disclosure of which is hereby incorporated herein by reference.

The elastic members are secured to the diaper 400 in an elastically contractible condition so that in a normally unrestrained configuration, the elastic members effectively contract or gather the diaper 400. The elastic members can be secured in an elastically contractible condition in at least two ways. For example, the elastic members can be stretched and secured while the diaper 400 is in an uncontracted condition. Alternatively, the diaper 400 can be contracted, for example, by pleating, and the elastic members secured and connected to the diaper 400 while the elastic members are in their unrelaxed or unstretched condition. The elastic members may extend along a portion of the length of the diaper 400. Alternatively, the elastic members can extend the entire length of the diaper 400, or any other length suitable to provide an elastically contractible line. The length of the elastic members is dictated by the diaper design.

The elastic members can be in a multitude of configurations. For example, the width of the elastic members can be varied from about 0.25 millimeters (0.01 inches) to about 25 millimeters (1.0 inch) or more; the elastic members can comprise a single strand of elastic material or can comprise several parallel or non-parallel strands of elastic material; or the elastic members can be rectangular or curvilinear. Still further, the elastic members can be affixed to the diaper in any of several ways which are known in the art. For example, the elastic members can be ultrasonically bonded, heat and pressure sealed into the diaper 400 using a variety of bonding patterns or the elastic members can simply be glued to the diaper 400.

The absorbent core 406 of the diaper 400 is positioned between the topsheet 404 and the backsheet 402. The absorbent core 406 can be manufactured in a wide variety of sizes and shapes (e.g., rectangular, hourglass, asymmetrical, etc.). The total absorbent capacity of the absorbent core 406 should, however, be compatible with the design liquid loading for the intended use of the absorbent article or diaper. Further, the size and absorbent capacity of the absorbent core 406 can vary to accommodate wearers ranging from infants through adults.

As shown in FIG. 17, the absorbent core 406 includes a fluid distribution member 408. In a preferred configuration such as depicted in FIG. 17, the absorbent core 406 preferably further includes an acquisition layer or member 410 in fluid communication with the fluid distribution member 408 and located between the fluid distribution member 408 and the topsheet 404. The acquisition layer or member 410 may be comprised of several different materials including nonwoven or woven webs of synthetic fibers including polyester, polypropylene, or polyethylene, natural fibers including cotton or cellulose, blends of such fibers, or any equivalent materials or combinations of materials.

In use, the diaper 400 is applied to a wearer by positioning the back waistband region under the wearer's back, and drawing the reminder of the diaper 400 between the wearer's legs so that the from waistband region is positioned across the front of the wearer. The tape-tab or other fasteners are then secured preferably to outwardly facing areas of the diaper 400.

ANALYTICAL METHODS

The following are representative analytical methods which have been found suitable for and useful in determining the performance of fluid transport webs in accordance with the present invention. The analytical methods described herein are preferably accomplished utilizing a particular standard fluid referred to as artificial menstrual fluid (hereafter referred to as "AMF"), although similar analytical studies could be undertaken with other fluids. Formulation and preparation of a suitable artificial menstrual fluid are described in the Test Methods section of allowed, commonly-assigned, co-pending U.S. patent application Ser. No. 08/141,156, filed Oct. 21, 1993 in the names of Richards et at., the disclosure of which is hereby incorporated herein by reference.

1. Acquisition Rate.

Acquisition rate, as utilized herein, is a measure of the time required for a given volume of surface-applied liquid to enter, or "strikethrough", a topsheet material into an underlying absorbent structure. In the present series of tests it is a measure of the time in seconds to completely drain 7.5 milliliters of AMF solution having a surface tension of 46–58 dynes/cm from a one inch diameter by ⅝ inch deep cavity having a multiplicity of holes in its lowermost surface. Other suitable fluid volumes include 17 milliliters and 5 milliliters. The cavity is integrally formed in a 4 inch×4 inch strikethrough plate which is placed on a complete absorbent article fabricated in accordance with the description above including the topsheet to be tested. The wearer-contacting surface of the topsheet sample is oriented face-up. An electric timer is started by the AMF solution contacting a pair of spaced electrodes in the aforedescribed cavity. The timer automatically shuts off when all of the AMF solution has drained from the cavity and into the absorbent element. Times are reported in seconds.

2. Dryness.

Dryness, as utilized herein, is a measure of how readily fluid can migrate upward onto the wearer-contacting surface of the topsheet after fluid acquisition, as well as residual wetness on the topsheet surface. Accordingly, 90 seconds after the completion of the AMF acquisition in the above acquisition rate test, the strikethrough plate is removed and a preweighed sample of filter paper approximately 5 inches×5 inches is inserted over the uppermost surface of the topsheet of the absorbent article sample, and a predetermined pressure loading of 0.25 psi. is applied to the sample for a period of 30 seconds. The filter paper is then removed and reweighed, and the amount of fluid absorbed by the filter paper is termed the "surface wetness" of the sample. Results are expressed in grams of fluid absorbed by the filter paper. Other suitable time increments include 20 minutes after completion of the AMF acquisition. As should thus be apparent, a lower "surface wetness" number is indicative of a dryer surface feel. More conveniently, "dryness" may be expressed as 1/surface wetness, which results in larger dryness values equating to dryer surface feel.

3. Masking.

As utilized herein, the term "masking" is defined as the difference in intensity of reflected light between a "used" or soiled product and its initial intensity reading before use. The acceptance of a catamenial product strongly depends on the masking performance of its topsheet. In fact, good masking not only provides a cleaner and drier topsheet surface but also reflects better absorbency and less rewet of the product. Masking may be analyzed by measuring the intensity of light reflected from the product's surface after it has been wetted, in order to be able to quantify it and compare results among different products.

The intensity of the light describes the energy of the light. The incoming (incident) light beam (e.g., sun light) is reflected by the surface and creates an outgoing (reflected) light beam that has a different energy or intensity. The difference of the intensities of the incoming and outgoing beam is the energy that the surface absorbs. For instance, a black surface absorbs significantly more energy or light than a white surface. The energy that is absorbed by the black surface may be transformed in heat. Therefore, black cars tend to be warmer than white cars in the summer. The intensity of the light strongly depends on the light source. Typically the intensity of the light may be characterized using different gray levels. Hence, white would acquire a value equal zero (white=0) and black the value 255 (black=255). Any gray (or intensity of the light) between these two values will be anywhere 0 and 255.

A sample product for evaluation is analyzed before introduction of any fluid, i.e., in its unused condition. A measurement area is defined and a set of measurements is taken. Results from 5 measurements are averaged. The samples are then infused with 5 ml of fluid in accordance with the procedure enunciated with regard to the acquisition test to perform the wet measurement. Before removing the strikethrough plate and subjecting the sample to the masking measurement and analysis, 3 minutes is allowed to elapse for the fluid to reach a steady state orientation within the sample. A second set measurements is then taken of the same product using the same identified measurement area. Results from 5 measurements are averaged. The numerical difference between the average initial reading and the average after-use reading provides a quantification of the difference in reflected light, and hence the cleanliness of the surface of the product. Low numerical differences reflect little change from pre-use condition, and hence effective "masking", while higher differences reflect a greater change from pre-use condition and hence less effective "masking".

The following is a description of suitable components and a suitable method for assessing masking performance of a fluid transport web according to the present invention.

Hardware components

The scanner utilized is a conventional HP Scanner IIp connected to an Apple Macintosh computer. The computer should have at least 8 MB RAM memory in order to be able to run the scanner software and NIH Image at the same time. The monitor should have at least 256 gray levels to run the software.

Software components

Scanner software (DeskScan II 2.1)

This software is provided by HP and designed to run with the HP Scanner IIp.

NIH Image Version 1.44

This program allows individuals to analyze a picture and determine the density of any color or gray level and the intensity of reflected light.

Measuring Procedures

The following describe in detail the procedure for measuring a catamenial pad or a similar object.

Data Determination

The flatness of the sample's surface is very important, in order to get consistent results. At this point, a 12" metal ruler weighing 42.8 grams is placed on the length of the catamenial to flatten the sample sufficiently to perform the measurements without unduly compressing or distorting the sample.

After scanning wet samples the screen is cleaned with an alcohol-impregnated soft tissue. The scanner screen must always be very clean, since dirt on the screen may affect the quality of a scanned sample and the measurement.

Using the scanner

Following steps are necessary to scan a sample with the HP IIp scanner:

Preparing the scanner:
1. Make sure the scanner is plugged into the computer
2. Start the computer
3. Switch on the scanner
4. Start the Scanner software program (DeskScan II 2.1)

Scanning an image:
5. Place the pad on the center of the screen
6. Place the weight (e.g., a metal ruler) on the pad.
7. Press PREVIEW on the menu of the program
8. Select the type of image you want to have. (Choose: Black and white photo!!)
9. Select the print path (Choose: Linttonic)
10. Select the area you want to save into a file.
11. Adjust the brightness and contrast
    Brightness: 114
    Contrast: 115

These values must be set, in order to have always the same quality of the image

12. Make sure that you have all the correct settings
13. Push the FINAL button

The system will ask you to define a name and a folder to store the file. The file should have a TIFF format. Usually this option is preset. But make sure you save the file in TIFF format, in order to be able to open this file in NIH Image.

The scanner will then scan your pad again, this time slower, because it saves the picture in a file.

Data evaluation

The following steps describe the procedure of analyzing a scanned picture.

Analyzing the scanned picture using NIH Image

Customizing the program
1. Open NIH Image.
2. Customize the program (only when you first use it!)
    a) Menu: OPTIONS
    Check Gray scale
    Preferences: Undo & Clipboard buffer: set to 1500K
        Record preferences in FILE menu
    b) Menu: ANALYZE
    Options: Check Area and Mean Density
        Digits right of . . . : set to 1
    c) Restart NIH Image to make all the settings effective Measuring
3. Open the calibration file named CALIBRATION.TIFF
4. Open the scanned file in TIFF format If the system warns you that the Undo Buffer is too small, add memory repeating preferences in step 2 a).

The measurements for the scanned file will be automatically calibrated, as long as the CALIBRATION.TIFF file is open at the same time. You can check if the picture has been calibrated, if there is a white diamond displayed in the title bar.

5. Go to ANALYZE in the menu and select RESET
6. Start measuring
    a) Select an area to be measured (you may choose a square box of about 0.4×0.4 in.) which is smaller than the area subjected to the fluid staining.
    b) Go to ANALYZE in the menu and select MEASURE
    c) Repeat steps 6 a) and b) for a total of 5 measurements of different sample "square boxes" within the region of interest.
    d) Go to ANALYZE in the menu and select SHOW RESULTS
7. Close the file without saving
8. Repeat steps 4–7 until you finished the measurements While particular embodiments of the present invention have been illustrated and described, it would be obvious to those skilled in the art that various other changes and modifications can be made without departing from the spirit and scope of the invention.

It is therefore intended to cover in the appended claims all such changes and modifications that are within the scope of this invention.

What is claimed is:

1. A method for selectively aperturing a nonwoven web exhibiting a plurality of surface energy gradients, said method comprising the steps of:
   (a) providing a nonwoven web of fibers exhibiting a surface energy, said nonwoven web having a first surface, a second surface and a plurality of fluid passageways placing said first and second surfaces in fluid communication with one another;
   (b) applying a surface treatment to the first surface of said nonwoven web, said surface treatment having a surface energy less than the surface energy of the fibers of said nonwoven web creating a plurality of surface energy gradients defined by discontinuous, spaced regions which are adapted to exert a force on a fluid contacting said first surface, such that said fluid will be directed toward said fluid passageways for transportation away from said first surface and in the direction of said second surface;
   (c) weakening the nonwoven web at a plurality of locations creating a plurality of weakened, melt-stabilized locations; and
   (d) applying a tensioning force to said nonwoven web to cause said nonwoven web to rupture at said plurality of weakened, melt-stabilized locations creating a plurality of apertures in said nonwoven web coincident with said plurality of weakened, melt-stabilized locations.

2. The method of claim 1, wherein said regions are also located at least partially within said fluid passageways.

3. The method of claim 1, wherein at least one fluid passageway exhibits a plurality of said regions located at least partially within said fluid passageway.

4. The method of claim 1, wherein said regions are randomly distributed over said first surface.

5. The method of claim 1, wherein said regions are randomly located at least partially within said fluid passageways.

6. The method of claim 5, wherein said regions are randomly located between said first and second surfaces.

7. The method of claim 1, wherein said regions are located within said fluid passageways at random distances from said first surface.

8. The method of claim 1, wherein at least one fluid passageway exhibits a plurality of said regions located at different distances from said first surface.

9. The method of claim 1, wherein said regions are located at least partially on said first surface and extend at least partially into said fluid passageways.

10. The method of claim 1, wherein said first surface exhibits a first surface energy and said second surface exhibits a second surface energy which is greater than said first surface energy.

11. The method of claim 1, wherein said surface treatment comprises a curable silicone material.

12. The method of claim 1, wherein said surface treatment comprises a fluoropolymer.

13. The method of claim 1, wherein said surface energy gradients are defined by boundaries between said discontinuous, spaced regions and materials having diverse surface energy characteristics.

14. The method of claim 1, wherein said nonwoven web is a web selected from the group consisting of a bonded carded web of fibers, a web of spunbonded fibers, a web of meltblown fibers, a multilayer material including at least one of said webs.

15. A nonwoven web made according to the method of claim 1.

16. The nonwoven web of claim 15, wherein said nonwoven web comprises a topsheet on an absorbent article.

17. The nonwoven web of claim 15, wherein said wherein said nonwoven web comprises a topsheet on a catamenial pad.

18. The nonwoven web of claim 15, wherein said wherein said nonwoven web comprises a topsheet on a diaper.

19. A method for selectively aperturing a nonwoven web exhibiting a plurality of surface energy gradients, said method comprising the steps of:

(a) providing a nonwoven web of fibers exhibiting a surface energy, said nonwoven web having a first surface, a second surface and a plurality of fluid passageways placing said first and second surfaces in fluid communication with one another;

(b) applying a surface treatment to the first surface of said nonwoven web, said surface treatment having a surface energy less than the surface energy of the fibers of said nonwoven web; and (c) weakening the nonwoven web at a plurality of locations creating a plurality of weakened, melt-stabilized locations; and (d) applying a tensioning force to said nonwoven web to cause said nonwoven web to rupture at said plurality of weakened, melt-stabilized locations creating a plurality of apertures in said nonwoven web coincident with said plurality of weakened, melt-stabilized locations.

20. The method of claim 19, wherein said surface treatment is also located at least partially within said fluid passageways.

21. The method of claim 19, wherein said surface treatment is are randomly distributed over said first surface.

22. The method of claim 19, wherein said first surface exhibits a first surface energy and said second surface exhibits a second surface energy which is greater than said first surface energy.

23. The method of claim 19, wherein said nonwoven web is a web selected from the group consisting of a bonded carded web of fibers, a web of spunbonded fibers, a web of meltblown fibers, a multilayer material including at least one of said webs.

24. The method of claim 19, wherein said surface treatment comprises a curable silicone material.

25. The method of claim 19, wherein said surface treatment comprises a fluoropolymer.

26. A nonwoven web made according to the method of claim 19.

27. The nonwoven web of claim 26, wherein said nonwoven web comprises a topsheet on an absorbent article.

28. The nonwoven web of claim 26, wherein said wherein said nonwoven web comprises a topsheet on a catamenial pad.

29. The nonwoven web of claim 26, wherein said wherein said nonwoven web comprises a topsheet on a diaper.

* * * * *

UNITED STATES PATENT AND TRADEMARK OFFICE
CERTIFICATE OF CORRECTION

PATENT NO. : 5,658,639

DATED : August 19, 1997

INVENTOR(S) : J. J. Curro et al.

It is certified that error appears in the above-identified patent and that said Letters Patent is hereby corrected as shown below:

In Col. 2, line 31, "catastrophe" should read --catastrophic--.

In Col. 5, line 59, "dearly" should read --clearly--.

In Col. 6, line 54, "at." should read --al.--.

In Col. 6, line 55, "at." should read --al.--.

In Col. 8, line 3, "or" should read --of--.

In Col. 8, line 6, "rarity" should read --clarity--.

In Col. 9, line 48, the word "as" should be deleted.

In Col. 14, line 24, "Coming" should read --Corning--.

In Col. 15, line 15, "Coming" should read --Corning--.

In Col. 18, line 43, "leer" should read --left--.

In Col. 18, line 64, "top sheet" should read --topsheet--.

In Col. 20, line 8, "at." should read --al.--.

In Col. 24, line 64, "top sheet" should read --topsheet--.

In Col. 25, line 29, "(0.5 mil" should read --(0.5 mil)--.

In Col. 26, line 6, "comers" should read --corners--.

In Col. 27, line 10, "from" should read --front--.

In Col. 27, line 28, "at." should read --al.--.

In Col. 28, line 56, "8 MB" should read --8MB--.

In Col. 29, line 28, "Linttonic" should read --Lintronic--.

In Col. 29, line 52, "1500K" should read --1500 K--.

In Col. 29, line 56, "Digits right of" should read --Digits right of--.

UNITED STATES PATENT AND TRADEMARK OFFICE
CERTIFICATE OF CORRECTION

PATENT NO.  : 5,658,639
DATED       : August 19, 1997
INVENTOR(S) : J. J. Curro et al.

It is certified that error appears in the above-identified patent and that said Letters Patent is hereby corrected as shown below:

In Col. 29, line 61, "Undo Buffer" should read --Undo Buffer--.

Signed and Sealed this

Tenth Day of November 1998

*Attest:*

BRUCE LEHMAN

*Attesting Officer*   Commissioner of Patents and Trademarks